(12) United States Patent
Wauters et al.

(10) Patent No.: US 9,643,998 B2
(45) Date of Patent: May 9, 2017

(54) REAL TIME MONITORING AND CONTROL OF PROTEIN PRODUCTION PROCESSES USING IMPEDANCE SPECTROSCOPY

(75) Inventors: Cary N. Wauters, La Crescenta, CA (US); Alexander Zaydenberg, Woodland Hills, CA (US)

(73) Assignees: BAXALTA GMBH, Opfikon (CH); BAXALTA INCORPORATED, Bannockburn, IL (US)

( * ) Notice: Subject to any disclaimer, the term of this patent is extended or adjusted under 35 U.S.C. 154(b) by 1406 days.

(21) Appl. No.: 13/315,376

(22) Filed: Dec. 9, 2011

(65) Prior Publication Data

US 2012/0153221 A1 Jun. 21, 2012

Related U.S. Application Data

(60) Provisional application No. 61/423,891, filed on Dec. 16, 2010.

(51) Int. Cl.
| | | |
|---|---|---|
| *C07K 1/30* | (2006.01) | |
| *C07K 1/34* | (2006.01) | |
| *G01N 27/02* | (2006.01) | |
| *C07K 1/24* | (2006.01) | |
| *G01R 27/00* | (2006.01) | |

(52) U.S. Cl.
CPC .................. *C07K 1/30* (2013.01); *C07K 1/24* (2013.01); *C07K 1/303* (2013.01); *G01N 27/021* (2013.01); *C07K 1/34* (2013.01); *G01R 27/00* (2013.01); *Y10T 436/115831* (2015.01); *Y10T 436/12* (2015.01); *Y10T 436/25375* (2015.01)

(58) Field of Classification Search
None
See application file for complete search history.

(56) References Cited

U.S. PATENT DOCUMENTS 5,447,440 A * 9/1995 Davis et al. ............. 435/6.16
2004/0223967 A1 * 11/2004 Kaibara et al. ......... 424/145.1
2007/0240505 A1 10/2007 Cammarata et al.

FOREIGN PATENT DOCUMENTS

WO WO 2008/135930 A1 * 11/2008

OTHER PUBLICATIONS

Sanabria, H. et al. "Impedance Spectroscopy of α-β Tubulin Heterodimer Suspensions," Biophysical Journal, vol. 90, Issue 12, Jun. 15, 2006, pp. 4644-4650.*
Baxter International, Inc., "Notification of Transmittal of the International Search Report and the Written Opinion of the International Searching Authority, or the Declaration," for PCT/US2011/064069, dated Mar. 2, 2012, 8 pages.

* cited by examiner

*Primary Examiner* — Yelena G Gakh
*Assistant Examiner* — Michelle Adams
(74) *Attorney, Agent, or Firm* — Kenneth H. Sonnenfeld; Margaret B. Brivanlou; King & Spalding LLP

(57) ABSTRACT

Methods and systems for monitoring and/or controlling protein separation, purification, extraction, and/or fractionation processes are provided. The impedance of a protein mixture undergoing a protein process is measured and compared to a target reference impedance value or range of reference impedance values. If the measured impedance is not within an acceptable deviation of the target reference impedance value, a parameter of the protein mixture or process is adjusted.

47 Claims, 17 Drawing Sheets

REAL TIME MONITORING AND CONTROL OF PROTEIN PRODUCTION PROCESSES USING IMPEDANCE SPECTROSCOPY

CROSS-REFERENCES TO RELATED APPLICATIONS

This application claims priority to U.S. Provisional Application Ser. No. 61/423,891, filed Dec. 16, 2010, the contents of which are incorporated herein by reference in its entirety.

FIELD OF INVENTION

The invention relates generally to electrochemical impedance spectroscopy and more specifically to methods of in-process monitoring, adjusting and/or controlling of protein suspension preparation processes and/or processes of protein separation from biologic fluids using electrochemical impedance spectroscopy.

BACKGROUND

Blood plasma proteins serve a wide variety of functions in the human body such as the maintenance of blood volume, osmotic pressure, viscosity, and other important physical parameters of blood. A number of commercial processes have been implemented to separate and purify these proteins from blood plasma for therapeutic use. Some common methods for protein purification include precipitation with ammonium sulfate and similar salts, organic solvent precipitation with cold ethanol or acetone and other such alcohols and ketones, selective adsorption on gels, isoelectric precipitation, and chromatography by use of adsorbents. Still other processes for selectively fractionating and purifying blood proteins involve the use of amino acids, water-soluble organic polymers, and water-insoluble polyelectrolyte polymers containing basic amino groups.

Many protein extraction and purification techniques are based on altering the solubility of a desired protein in a biologic fluid such as blood plasma or a plasma solution by adjusting any of number of properties of the protein solution. Through the addition of salts or dilution of a solution, separation may be carried out in the range of low ionic strengths at which the interactions of proteins with electrolytes differ from each other, both in the isoelectric condition and when dissociated as acids or bases. The solubility of a protein may also be reduced by the addition of alcohols, acetone or other water miscible organic solvents to protein solutions. The balance between the precipitating action of alcohols and the salt interactions permits attainment of a variety of conditions under which the protein to be separated may be brought to a desired solubility. This balance may be altered based on the pH and temperature for each protein component; however, to avoid denaturing of the desired protein, sufficiently low temperatures should be maintained. Moreover, the pH may be controlled by adding a buffer such as an acetate or other buffers of known ionic strength, and adjusted so as to take advantage of the differences in the isoelectric points and the directions of the interactions with salts of the protein components to be separated. Finally, the concentration of protein may be maintained as low as possible to obtain a desired amount of protein precipitate to minimize protein-protein interactions. As the number of components in the solution or suspension increases or if multiple components have similar physical chemical properties, more of these variables must be accurately controlled to lower the solubility of a single protein type.

Because these extracted and/or purified plasma proteins may be used therapeutically in humans, such extraction and purification processes require rigorous quality control, such as monitoring and analytical testing of the biologic fluid to ensure that the end-product is both consistent and safe, and that the chemical properties of the mixture are kept consistent with the intended process design. For example, conventional monitoring techniques such as the use of enzyme-linked immunosorbent assays ("ELISAs") or Surface Plasmon resonance may be used to determine the amount of antibody activity in a prepared sample. Other common monitoring methods such as reversed-phase, affinity or cation-exchange chromatography require the preparation of samples and controls and incubating for a certain period of time to monitor protein degradation. Additionally, SDS-Page electrophoresis techniques can be used to determine antibody impurities.

Unfortunately, many of these known monitoring and control techniques are costly and may require specialized antigens, reagents and equipment to perform the requisite analyses. In fact, many of these known techniques are unsuitable for monitoring and controlling separation processes in real-time, as they require sample preparation, specific incubation times and/or other time-consuming steps.

A need therefore exists for Process Analytical Technology (PAT) methods and systems for in-process monitoring of suspensions and solutions in an improved manner that may enhance protein process understanding, improve process control, and/or achieve consistent product quality. As used herein, PAT includes, for example, a system for designing, analyzing, and/or controlling manufacturing through timely measurements (i.e., during processing) of critical quality and performance attributes of raw and in-process materials and processes with the goal of ensuring final product quality. It would be beneficial if these desired attributes were obtainable using a method that is fast, reliable, low maintenance and involves an ease in the use of equipment, such as the use of equipment that does not need to be dismantled or the use of sensors that are easily cleaned.

SUMMARY OF THE INVENTION

It has been found that Impedance Spectroscopy (IS) may be used to characterize the electrical and/or electrochemical properties of many types of protein solutions, suspensions and colloids, including biologic fluids such as blood plasma, blood plasma fractions and blood plasma solutions. Exemplary embodiments described herein utilize IS for fast and reliable in-process monitoring and/or control of process parameters during protein solution preparation processes, protein extraction processes, protein purification processes, and/or protein fraction storage processes.

As described below, certain embodiments of the invention allow for the measurement of the impedance of a protein-containing mixture involved in a protein process. Such impedance measurements may be used to determine and/or control a parameter of the mixture and/or protein process by comparison to a reference impedance value or reference range of impedance values, without the need to slow or stop the process. The disclosed systems and methods, therefore, may improve process control capabilities, facilitate timely process adjustments and/or may assist in the preparation of product having consistent quality by allowing a practitioner real-time or near real-time access to information about properties of protein-containing mixtures, without the need for sample preparation or other time-consuming testing procedures.

One aspect of the invention is to provide a method for separating a protein from a biologic fluid. A parameter that modifies the solubility of a protein in a biologic fluid may be adjusted and the impedance of the biologic fluid may be monitored before, during and/or after the adjusting of the parameter. The impedance of the biologic fluid may be compared to a target impedance value, which may correspond to a target degree of separation of the protein from the biologic fluid. The parameter that modifies solubility may be further modified when the impedance deviates from the target impedance value by more than an acceptable tolerance. The further modification may include determining an amount of modification of the parameter that would be needed to cause the impedance of the biologic fluid to be at or about the target impedance value and, optionally, modifying the parameter by that amount. It will be appreciated that in some aspects of the invention the modification of the parameter is not optional. Further, the modification may be manual or automatic. Exemplary biologic fluids may be blood plasma, fractionated plasma intermediates, protein solutions, protein suspensions, and/or strained cell culture suspensions.

In another aspect of the invention, a method for preparing a protein suspension having an impedance within a target reference range of impedance values is provided. A protein solid and/or paste may be admixed with a solvent to form a protein suspension. The impedance of the protein suspension may be monitored before, during, and/or after the admixing step and the impedance may be compared to a target reference range of impedance values and/or a single target reference impedance value. The admixing, monitoring and comparing steps may be repeated until the impedance is within the target reference range of impedance values and/or the impedance is within an acceptable amount of the single target reference impedance value.

In another aspect of the invention, a process control system for controlling separation of a protein from a biologic fluid in a vessel is provided. The system may comprise an impedance meter, which may be adapted for measuring the impedance of a biologic fluid. The impedance meter may comprise two or more electrodes. The two or more electrodes may comprise a first electrode or first pair of electrodes capable of transmitting an electrical signal through the biologic fluid and a second electrode or second pair of electrodes capable of receiving the electrical signal from the first pair of electrodes. The first pair of electrodes may be configured to be inserted into a first port of the vessel and the second pair of electrodes may be configured also to be inserted into the first port or a second port of the vessel. Additionally, the system may further comprise a computer electrically connected to the impedance meter. The computer may be adapted to retrieve a measurement of impedance of the biologic fluid from the impedance meter and/or may be adapted to automatically adjust a parameter that modifies the solubility of a protein in the biologic fluid when the impedance measurement deviates from a target impedance value and/or a target reference impedance range by more than an acceptable tolerance.

In yet another aspect of the invention, a process control system for preparing a protein suspension in a reactor in a protein separation process is provided. The system may comprise an impedance meter for measuring an impedance of the protein suspension. The impedance meter may comprise two or more electrodes, including a first pair of electrodes capable of transmitting an electrical signal through the protein suspension. The first pair of electrodes may be configured to be inserted into a first reactor port of the reactor. The impedance meter may further comprise a second pair of electrodes for receiving the electrical signal from the first electrode. Generally, the second pair of electrodes may be configured to be also inserted into the first reactor port or a second reactor port of the reactor. The system may further comprise a computer electrically connected to the impedance meter. The computer may be adapted to retrieve a measurement of impedance of the protein suspension from the impedance meter, and automatically trigger a subsequent step in the protein separation process when the measurement is within a target reference range of impedance values.

Another aspect of the invention is to provide a method for monitoring a protein separation process. The method may comprise measuring the impedance of a protein suspension at a plurality of frequencies to produce a measured impedance spectrum. This measured impedance spectrum may be contrasted or compared to a known impedance spectrum, or reference impedance spectrum. Based on the comparison, at least one physical or chemical property of the protein solution may be characterized and a modification may be made to the protein solution and/or the protein separation process. This modification may be said to be based on the characterization of the physical or chemical property.

Another aspect of the invention is to provide a method of monitoring a protein purification process. The method comprises measuring the impedance of a protein-containing mixture such as a blood plasma solution or suspension at a defined frequency or range of frequencies and comparing the measured impedance to a reference impedance to determine at least one characteristic of the protein purification process.

Additional features and advantages of embodiments will be set forth in the description which follows, and in part will be apparent from the description. The objectives and other advantages of the invention will be realized and attained by the system and methods particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

DETAILED DESCRIPTION

Figure 1:
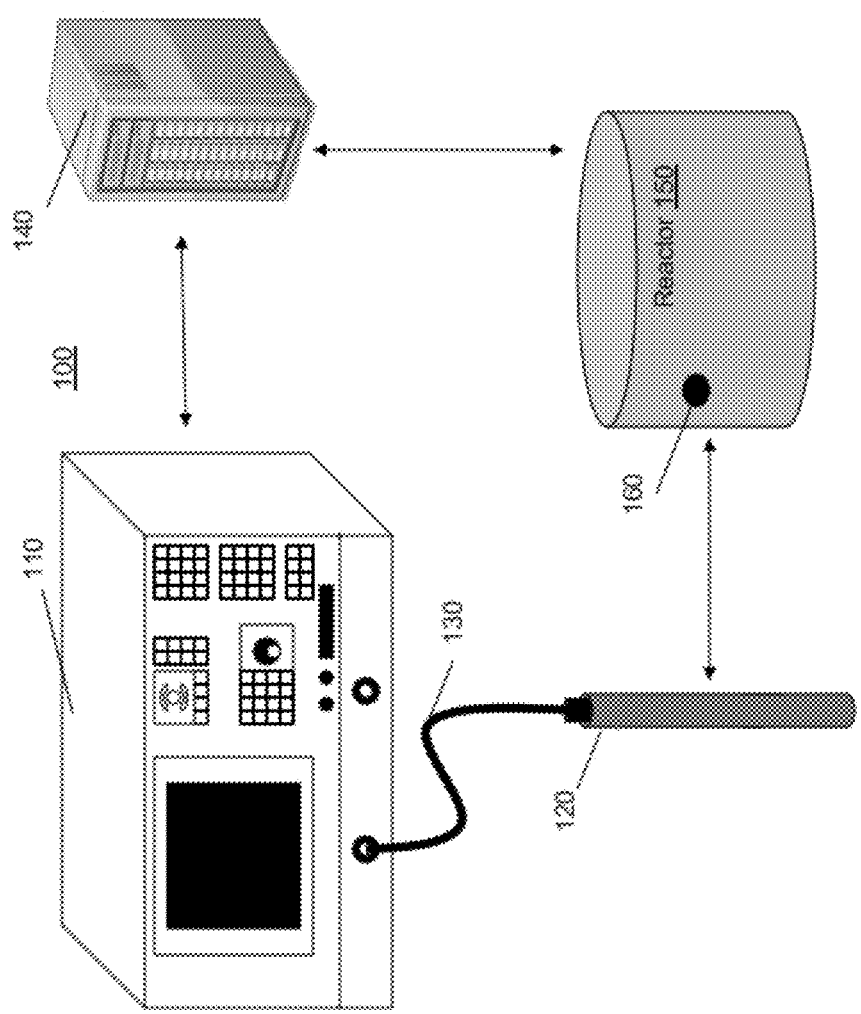
FIG. 1 shows an exemplary embodiment of a process control system of the present invention for controlling and/or monitoring a protein process.

All terms used herein are intended to have their ordinary meaning in the art unless otherwise provided. All concentrations are in terms of percentage by volume of the specified component relative to the entire volume of the mixture. Unless otherwise specified, the term "mixture" may refer to a solid, liquid, solution, suspension or colloid comprising at least two substances. The term "protein mixture" is defined as a mixture comprising at least one protein. In some embodiments the "protein mixture" may refer to a "biologic fluid" such as, but not limited to blood plasma, pooled plasma, plasma mixtures, fractionated plasma products, fractionated plasma intermediates, protein solution or suspension, cell culture suspension, or any combination thereof. As used herein, pooled plasma may refer to a component of whole blood collected from any number of donors and combined. In certain embodiments pooled plasma may be collected from about 200 donors, about 500 donors, about 1000 donors, about 2,000 donors, or about 5,000 or more.

The invention generally provides systems and methods that allow for real-time or near real-time monitoring and/or control of protein processes that utilize or create protein mixtures. As used herein, the term "protein process" includes any of a number of commercial processes, such as but not limited to protein separation processes, protein purification processes, protein extraction processes, protein fractionation processes, protein formulation, protein mixture production, protein mixture storage, protein fraction storage, protein paste storage, protein final container storage and the like.

Exemplary protein processes include, but are not limited to, the protein processes described in *J. Am. Chem. Soc.* 68:459-475 (1946), Cohn et al. (the "Cohn Fractionation Process" or "Cohn Process"), incorporated herein by reference in its entirety; *J. Am. Chem. Soc.* 71:541-550 (1949), Onlcey et al. (the "Oncley Fractionation Process" or "Oncley Process"), incorporated herein by reference in its entirety; *Vox Sang.* 7:414-424 (1962), Kistler et al. (the "Kistler Fractionation Process" or "Kistler Process"), incorporated herein by reference in its entirety; and *Vox Sang* 92:42-44 (2007), Teschner et al. (the "Teschner Fractionation Process" or "Teschner Process), incorporated herein by reference in its entirety and any variations of these processes. It will be understood that the systems described herein, which use IS to monitor and/or control protein processes, are useful with any number of protein processes and, although a number of exemplary protein processes are described in detail herein, the invention is by no means limited to only those exemplary protein processes described. In fact, the systems described herein may be useful with any protein extraction and/or purification technique which is based on altering the solubility of a desired protein in a biologic fluid by adjusting ionic concentration, protein concentration, water miscible organic precipitant concentration (e.g., alcohol), pH, temperature and/or any combination thereof.

The term "fractionated plasma intermediate" refers to, but is not limited to Cohn Fraction I, Cohn Fraction II+III, Cohn Fraction I+II+III, Cohn Fraction IV-1, Cohn Fraction IV-4, and/or Cohn Fraction V, from the Cohn Fractionation Process; Oncley Fraction II+IIIw, Oncley Fraction II and/or Oncley Fraction III from the Oncley Fractionation Process; Kistler Precipitate A, Kistler Precipitate B, Kistler Precipitate IV, Kistler Precipitate C and/or Kistler Precipitate D from the Kistler Fractionation Process; Teschner Precipitate G from the Teschner Fractionation Process; and/or any combinations, modifications or variations thereof.

The term "fractionated plasma product" includes any protein or protein product separated from blood plasma, such as but not limited to, albumin, alpha1-proteinase inhibitor, antihemophilic factor, von Willebran factor complex, anti-inhibitor coagulant complex, antithrombin, C1 esterase inhibitor, coagulation factors, fibrin, fibrinogen, immunoglobulin, protein C concentrate, thrombin and/or a variety of combinations and variations thereof. Typically, a fractionated plasma product may be sufficiently sterile for administration to a human patient.

In certain embodiments of the invention, a parameter that modifies the solubility of a protein in a protein mixture undergoing a protein process is monitored, adjusted, and/or modified. Such parameters may include, for example: pH, conductivity, liquid/solid separation, water miscible organic precipitant concentration, protein aggregation, density, flow rate, viscosity, protein concentration, temperature and/or aging of proteins of mixtures.

Generally, the invention is directed to the monitoring and/or controlling of protein processes using impedance measurements of a protein mixture utilized or prepared by the processes. The instant invention allows for a protein mixture to be characterized at any stage of a protein process without the direct measurement of specific properties. Rather, the impedance of a protein mixture may be measured during the protein process, in real-time or near real-time, and these impedance measurements may be used to indirectly determine properties or parameters of the mixture or the process about which information is desired. Using the information obtained, the process or mixture may be adjusted. The disclosed systems and methods, therefore, may improve process control capabilities, facilitate timely process adjustments and/or may assist in the preparation of product having consistent quality by allowing a practitioner real-time or near real-time access to information about properties of protein-containing mixtures, without the need for sample preparation or other time consuming testing procedures. By "near real-time" it is meant that the process can be monitored and/or adjusted within a time frame such that the properties of the process have not changed by a measurable and/or significant amount. For example, "near real-time" may be within 1 second, 5 seconds, 10 seconds, 20 seconds, 30 seconds, 1 minute, 2 minutes, 5 minutes, 10 minutes, or 15 minutes, depending on the protein process and/or protein mixture. Preferably "near real-time" may be within 1 second, 5 seconds, 10 seconds, 20 seconds, 30 seconds, or 1 minute.

Exemplary embodiments described herein utilize IS for fast and reliable in-process monitoring and/or control of protein process parameters during such protein processes as: protein solution preparation processes, protein extraction processes, protein purification processes, and/or protein fraction storage processes. In certain embodiments, any number of measurements of the complex impedance of a protein-containing mixture involved in a protein process may be obtained, for example, using an electrical probe in electrical contact with the protein mixture. Such impedance measurements may be used to determine a parameter or state of the mixture at any step of a protein process by comparison to a reference impedance value or reference range of impedance values. The reference impedance value or reference range of impedance values may be previously measured or determined for a substantially similar protein mixture during a substantially similar protein process.

In certain embodiments, if the measured impedance value is within an acceptable tolerance of the reference impedance value or reference range of impedance values, the protein process is allowed to continue without adjustment or modification. However, if the measured impedance value deviates from the reference impedance value or reference range of impedance values by more than an acceptable tolerance, an adjustment may be made to the protein process and/or protein mixture.

It will be understood that the acceptable tolerance will depend on any number of parameters including but not limited to the particular protein process or step within the process, the specific protein mixture, the desired final product and the like. Moreover, the acceptable tolerance will vary depending on the correlation between impedance values of the protein mixture to physical chemical characteristics of the protein mixture. In some exemplary embodiments, the acceptable tolerance may be from about a 0.001% to about a 10%, from about a 0.01% to about a 5%, or from about a 0.1% to about 1% difference between the measured impedance value and the reference impedance value. In certain embodiments, the acceptable tolerance may be less than or equal to 0.5%, 1%, 1.5%, 2%, 3%, 4%, 5%, 6%, 7%, 8%, 9% or 10% of the reference impedance values. In other embodiments, the acceptable tolerance may be at or within a standard deviation, two standard deviations, or within a standard error of the empirical data used to obtain the reference impedance values.

In other embodiments, the impedance of a protein mixture may be determined in real-time or near real time for any reasonable duration including throughout each process step of a protein process using the protein mixture. If at any time during the protein process the measured impedance value is determined to be outside a desired or "target" range of reference impedance values, a change or adjustment may be effected on the protein mixture or protein process. In some embodiments, the change or adjustment may be automatic and/or computerized, while in others the change or adjustment may be manual. In other embodiments, the measuring the impedance of the mixture, comparing the measured impedance value to a reference range of impedance values, and effecting a change or adjustment to the protein mixture or process may be continued or repeated as desired or required until the measured impedance is within the target range of reference impedance values.

In one exemplary embodiment, a change or adjustment may be made to a parameter that modifies the solubility of a protein in the protein mixture. A parameter that modifies a protein in a protein mixture may be, for example: solute concentration, solvent concentration, pH, ionic strength and/or temperature. It will be appreciated that there are any number of methods to change or modify such a parameter or a combination of parameters of a protein mixture, such as, for example: the addition of components such as salts, alcohols, water, acids and/or bases to the protein mixture; the removal of components from the protein mixture by, for example, filtration or the like; the heating and/or cooling of the protein mixture; and/or the exposure of the protein mixture to external sources of energy.

In another exemplary embodiment, the desired or target reference impedance value or target range of reference impedance values may be correlated to any number of physical and/or chemical properties of a protein mixture. The impedance of a protein suspension may be determined at many stages of a protein process, such as a protein extraction, separation or purification process, which uses the protein suspension. By correlating the measured impedance values to a characteristic, such as, for example: protein concentration, salt concentration, degree of protein degradation (e.g., degradation activity of the protein including but not limited to: binding activity, enzymatic activity, antigen/antibody activity, etc.), protein aging, and/or degree of protein separation, each impedance measurement will allow for an approximation of that characteristic. In this way, information about the process may be obtained, and changes to the process may be effected based on the information.

Although described as a measured impedance value, it will be appreciated that any number of measured impedance values may be obtained from a protein mixture as desired or required to determine the impedance of a protein mixture to a certain degree of certainty. The measurements may be taken at any time intervals up to and including continuous measurements. Moreover, the impedance of a protein mixture, such as but not limited to a protein precipitate, may be determined at multiple locations within the protein mixture to ensure homogeneity. This is important in large-scale manufacturing processes where homogeneity of a solution or precipitate is more difficult to obtain. Further, during a single protein process, impedance measurements may be taken in-situ or ex-situ at any number of steps throughout. In this way, measured impedance values may be determined throughout an entire lot or batch of a protein mixture, instead of, for example, measuring a sample taken from the lot. However, if desired, the impedance of a sample may be measured.

Referring to FIG. 1, an exemplary process control system 100 is shown wherein the impedance of a protein mixture, such as a biologic fluid, contained within a reactor or vessel 150 may be measured at one or more frequencies during a protein process. As shown, the control system 100 generally includes an impedance meter 110 having a probe 120 attached thereto by any conductive means 130, such as insulated wires or the like. In another embodiment, the control system 100 may include a pair of probes 120 attached to the impedance meter 110. Although only one probe 120 is shown, it will be appreciated that any number of probes 120 may be attached to the impedance meter 110, including but not limited to 2, 3, 4, 5, 10, 15, or 20 probes, and such may be located throughout the reactor or vessel 150.

In certain embodiments, the impedance meter 110 may be any electronic instrument that is capable of outputting electrical signals and receiving electrical signals. The impedance meter 110 may generate an electrical signal at a certain voltage, current, and/or frequency through an attached probe 120 which may be disposed in a protein mixture in the reactor or vessel 150. The probe 120 may be adapted to be inserted into a reactor port 160 of the reactor or vessel 150 such that the probe 120 is in direct or indirect electrical contact with the biologic fluid contained therein. Again, although only a single reactor port 160 is shown, it will be appreciated that any number of reactor ports 160 may be present in the reactor or vessel 150, such as but not limited to 2, 3, 4, 5, 10, 15, 20, or 25 ports 160. Moreover, a single probe 120 may be inserted into a single reactor port 160. Alternatively, a pair of probes 120 or multiple probes 120 may be inserted into a single reactor port 160.

Generally, the impedance meter 110 may have the capability to produce and transmit a sinusoidal electrical signal of a frequency between about 20 Hz to about 20 MHz. In a preferred embodiment, the electrical signal generated may be from about 0.02 kHz to about 843 kHz. In another embodiment, the electrical signal generated may be from about 0.05 kHz to about 0.1 kHz. The impedance meter 110 may further have the capability to produce and transmit an AC electrical signal of from about 1 to about 500 mV, including any and all values therebetween, however, the electrical signal employed should cause only minimal perturbation of the mixture to produce a pseudo-linear current response. The impedance meter 110 may additionally receive an electrical signal once it has propagated through the mixture via the attached probe 120.

In certain embodiments, the impedance meter 110 is capable of measuring inductance, capacitance, resistance, and/or the real and imaginary components of impedance (further explained below) of a protein mixture by detecting differences in the electrical signal transmitted to the biologic fluid in the reactor or vessel 150 and the received or resulting signal after the electrical signal has propagated through the biologic fluid. In one exemplary embodiment, the impedance meter 110 may be an Agilent Technologies E4980A Precision LCR meter. In another exemplary embodiment, the impedance meter 110 may be an Agilent 4989 precision LCR meter.

As shown, the impedance meter 110 may be controllably and/or electrically connected to a computer 140 having memory to store and process data received from the impedance meter 110. The computer 140 may be connected to the impedance meter 110 by any means known in the art, including both wired connections and wireless connections over a network. Although not shown, the computer may be connected to any of a number of known peripheral devices including, for example, a keyboard, mouse, display, touch screen, printer, and/or any other equipment to facilitate user input and/or output. Alternatively, it is contemplated that the computer 140 and the impedance meter 110 may be integrated in a single device.

In one exemplary embodiment, the computer 140 is adapted to retrieve a measurement of impedance of a protein mixture from an impedance meter 110 having a probe 120 disposed in the protein mixture. The computer may be adapted to control the impedance meter 110 such as, for example, the output of an electrical signal.

In another exemplary embodiment, the computer 140 may be adapted to analyze and/or adjust a parameter of a protein mixture in the reactor or vessel 150. The parameter may modify the solubility of a protein in the protein mixture such that the protein may be precipitated out of the protein mixture. For example, the computer 140 may be controllably connected to additional electrical or mechanical process equipment (not shown) that may also be connected to the reactor or vessel 150. Exemplary process equipment includes but is not limited to equipment such as: pumps, valves, heating or cooling equipment, mixers, containers and the like. In this way, the computer 140 may be adapted to control process equipment which may adjust process parameters such as the rate of addition of an additive or the raising or lowering of the temperature. Although not shown, the computer 140 may be further connected to a warning system such as an audible alarm system and/or visual alert system.

In certain embodiments, the computer 140 may be adapted to adjust a parameter that modifies the solubility of a protein in a protein mixture when the measured impedance of a protein mixture deviates from a target reference impedance value or target range of reference impedance values by more than an acceptable tolerance. In one embodiment, the target reference impedance value or target range of reference impedance values may be stored in, for example, a database that may be accessed by the computer 140. The computer 140 may then compare measured impedance values received and/or stored from an impedance meter 110 to stored reference impedance values (i.e. target reference impedance values and target ranges of reference impedance values). Generally, the acceptable tolerance may be entered by a user or determined by the computer 140 based on information about a particular process, mixture, or desired product (e.g., data obtained from previous production processes, parameters from standard operating procedures for any particular process, mixture or desired product, etc.). The computer 140 may be further adapted to automatically warn an operator when the measured impedance of a protein mixture deviates from a target reference impedance value or target range of reference impedance values by more than an acceptable tolerance.

Although described as a reactor or vessel 150, it will be understood that the instant invention is not so limited and any equipment capable of containing and/or transferring a protein mixture for a desired amount of time is contemplated as being compatible with the instant invention. Therefore, the reactor or vessel 150 may be any piece of equipment such as, for example: one or more kettles, vats, tanks, bottles, bags, filters, centrifuges, sinks and/or any other compatible container. In one specific embodiment, the reactor or vessel 150 may be a transfer line containing the protein mixture and the transfer line may be made from a material such as for example, stainless steel, glass or plastic. In another embodiment, the reactor or vessel 150 may be a chromatography column such as but not limited to a gel filtration, ion exchange or immunoaffinity column. In yet another exemplary embodiment, the reactor or vessel 150 may be a chromatography column having, for example, a packed or expanded bed configuration. In other exemplary embodiments, the reactor or vessel 150 may be: a batch reactor, a semibatch reactor, a continuous-stirred tank reactor (CSTRs), a tubular reactor, a fixed bed reactor, or a fluidized bed reactor.

It will be understood that the reactor or vessel 150 may be located inside a processing room, or may be connected to the processing room by, for example, insulated stainless steel or glass-lined pipes. Moreover, in some embodiments, cooling and/or heating coils (not shown) are placed adjacent to or surround the reactor or kettle 150 of exemplary systems in order to increase the rate at which the temperature may be decreased.

Figure 2:
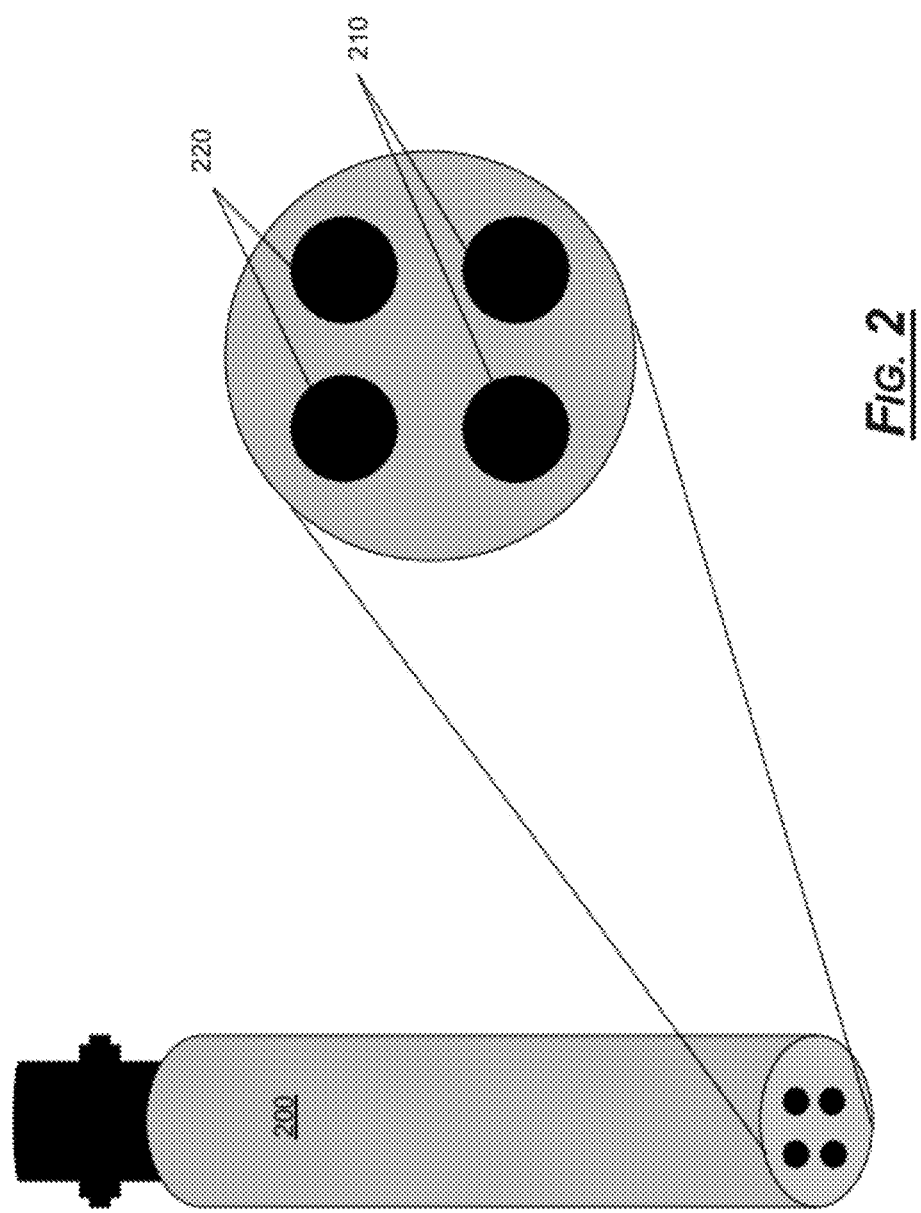
FIG. 2 shows an exemplary embodiment of a probe for use with the process control system of FIG. 1.

Referring to FIG. 2, an exemplary embodiment of a probe 200 is shown. The probe 200 may be connected to an impedance meter through any means known in the art, including but not limited to: wires, insulated wires, wireless technology, fittings, clamps, screws, clips, adhesives and the like. In one embodiment, the probe 200 comprises at least one transmitting electrode 210 and at least one receiving electrode 220. The at least one transmitting electrode 210 may be electrically connected to an impedance meter and adapted such that an electrical signal, or excitation signal, may be propagated from the impedance meter to the at least one transmitting electrode 210. The electrical signal may flow from the at least one transmitting electrode 210 contacted with, submersed, or disposed in a protein mixture, through the mixture, and may be received by at least one receiving electrode 220, which may also be contacted with, submersed, or disposed in the mixture. The at least one receiving electrode 220 may be adapted to receive an electrical signal, and may be electrically connected to an impedance meter such that an electrical signal may be transmitted from the at least one receiving electrode 220 to the impedance meter 210. Generally, the at least one transmitting electrode 210 may be insulated from the at least one receiving electrode 220 to prevent the electrodes from contacting each other. One exemplary probe 200 is an ABB Model TB457 Sterilizable Conductivity Sensor. In one exemplary embodiment, the at least one transmitting electrode 210 comprises a pair of electrodes and the at least one receiving electrode 220 also comprises a pair of electrodes.

It will be appreciated that a single probe 200 may comprise a pair of electrodes, or any number of transmitting 210 or receiving 220 electrodes and, although characterized as a transmitting electrode 210 and receiving electrode 220, any electrode may be adapted to be a receiving electrode, a transmitting electrode, or both a receiving and transmitting electrode depending on polarity. Moreover, it will be appreciated that any number of probes 200 may be employed to measure the electrochemical and electrical properties of a mixture, such as but not limited to impedance. Further, each probe 200 may be capable of emitting electrical signals at different frequencies or at the same frequency of any other probe 200.

In one exemplary embodiment, a single probe 200 may be submersed in a protein mixture, such as, for example, a blood plasma and the impedance of the plasma may be measured during a protein purification or separation process. In another example, two or more probes 200 may be submersed in multiple locations within a biologic fluid, such as but not limited to an albumin solution, and the impedance measurements may be taken at each location at the same excitation frequency. In yet another example, a single probe 200 may be used to measure the impedance of a protein suspension having a protein concentration, for example IgG concentration, at multiple frequencies and in real time.

Impedance Spectroscopy

In one aspect of the invention, the monitoring and/or controlling of protein processes may utilize any suitable methods and devices for measuring impedance of a protein mixture. In one exemplary embodiment, a sinusoidal electrical signal, or excitation signal, may be applied to any liquid, such as, for example, a protein solution or suspension. The signal may generally range from about 1 to about 100 mV such that the impedance measurement causes only minimal perturbation of the system. As shown in Equation 1, an exemplary excitation signal has a time-dependent potential, E(t), an amplitude, $E_0$, and a frequency, $\omega$. The radial frequency, $\omega$, is equal to the $2\pi$ multiplied by f, the frequency in hertz, i.e., $\omega = 2\pi f$.

$$E(t) = E_0 \sin(\omega t) \qquad \text{Equation 1}$$

Once the excitation signal propagates through the protein mixture, the resulting current may be measured to determine the impedance of the mixture. As shown in Equation 2, the measured current, I(t), may approximate a sinusoidal wave at the same frequency as the excitation signal, but shifted in phase.

$$I(t) = I_0 \sin(\omega t + \phi) \qquad \text{Equation 2}$$

where I(t) is the current at time t, with amplitude $I_0$ and shifted in phase by $\phi$.

Ohm's Law (Equation 3) may be used to express the impedance of the mixture at a particular time as a function of a magnitude $Z_0$, frequency ($\omega$), and a phase shift ($\phi$).

$$Z_t = \frac{E_t}{I_t} = \frac{E_0 \sin(\omega t)}{I_0 \sin(\omega t + \phi)} = Z_0 \frac{\sin(\omega t)}{\sin(\omega t + \phi)} \qquad \text{Equation 3}$$

Additionally, the impedance may also be represented in frequency space as a complex number having a real part (representative of resistance) and imaginary part (representative of reactance), as shown in Equation 4.

$$Z_\omega = \frac{E}{I} = Z_0 e^{j\phi} = Z_0(\cos\phi + j\sin\phi) \qquad \text{Equation 4}$$

Thus, the complex impedance will vary with the frequency of the excitation signal applied.

Because the complex impedance is represented by a real component and an imaginary component, either of these components may be determined from a complex impedance measurement of a protein mixture. Moreover, depending on a particular protein mixture being measured, either the real component or imaginary component may be more strongly correlated to a property, parameter, or state of the protein mixture than the other. Therefore, in one embodiment, either the real or the imaginary component of impedance may be independently compared to a reference impedance value to determine information about the protein mixture or protein process.

It will be further appreciated that the real and imaginary components of a measured impedance may be strongly correlated to properties of a protein mixture at the same frequency or at different frequencies. For example, the real component of the impedance of a protein suspension may be strongly correlated to a particular protein mixture or state of a protein mixture at a frequency of from about 1.6 kHz to about 16 kHz, while the imaginary component of the impedance of the same protein mixture may be strongly correlated to the protein mixture or state of the protein mixture at a frequency of from about 16 kHz to about 50 kHz.

While, in some embodiments, only the real or imaginary component of the impedance may be determined and compared to a reference impedance value, in other embodiments, the complex impedance, including both the real and imaginary components, may be measured and compared to a target reference impedance value or range of target reference impedance values.

Generating A Reference Curve

Once the impedance of a protein mixture is measured, the measured impedance value may be compared to a reference impedance value or range of reference impedance values. In particular, the reference impedance value or range of reference impedance values may represent target values for any step in a protein process such as a separation, extraction or fractionation process. The reference impedance value may be referred to as a "target impedance value" or "target reference impedance value," as any subsequent protein mixture desired to have a substantially similar composition to the reference mixture at the particular step in the protein process should have a substantially similar impedance if other variables remain unchanged.

In an exemplary embodiment, the reference impedance values or range of reference impedance values may be determined or ascertained via preliminary measurements and correlation of the impedance of a reference protein mixture subjected to a reference protein process. Both the reference protein mixture and reference protein process may be substantially similar to the subsequent non-reference protein mixture and non-reference protein processes about which information is desired such that the correlation will be accurate.

For example, the impedance of a reference protein mixture having known physical and chemical characteristics may be measured and recorded before the mixture is subjected to a reference protein process. The impedance of any subsequent, non-reference protein mixture may be compared to this reference impedance value to determine if the non-reference mixture is substantially similar to the reference mixture and thus suitable for a particular protein process.

In another example, a first step of a reference protein process may be carried out on the reference protein mixture and the impedance may be measured and recorded throughout the first step to obtain a reference impedance value and/or a range of reference impedance values that correspond to the first step of the reference process. During this first reference process step, one or more physical or chemical characteristic of the reference mixture may be carefully adjusted and measured in addition to the impedance recordation. Using linear and/or non-linear complex regression analysis or other mathematical techniques, the impedance of the reference mixture may be correlated to the specific, measured characteristics of the protein mixture during the first step of the process. Accordingly, the impedance of a substantially similar non-reference protein mixture undergoing a substantially similar non-reference process should be substantially similar to the reference impedance value or range of values obtained. The reference impedance value or range of reference impedance values may thus be referred to as a "target reference impedance value," "target impedance value" or "target reference range of impedance values."

It will be appreciated that this procedure of obtaining reference impedance values may be repeated as desired or required to obtain reference impedance values for multiple steps in a reference protein process. Likewise, this procedure may be repeated for any number of protein mixtures. Moreover, both the reference impedance values and measured protein mixture characteristic may be recorded in, for example, a database. In this way, it is possible to obtain any desired spectrum of reference impedance values based on the characteristic of a protein mixture and/or a particular step in a protein process.

In a more preferred embodiment, reference impedance values or a range of reference impedance values may be determined via correlation and extrapolation, rather than actual measurement of each data point. For example, a discrete number of reference impedance values may be measured for a protein mixture having known parameters. Generally, one or more parameters of the protein mixture may be adjusted to another known value, and additional impedance measurements may be ascertained. Using analytical techniques such as linear and/or non-linear regression analysis, the real and/or imaginary part of the impedance of the protein mixture may be correlated to the adjusted parameter or parameters. In this way, a regression equation may be determined, wherein the regression equation may be used to predict further data points. It will be understood that such correlation and extrapolation may be computed in any number of ways known in the art, and such calculations may be carried out by statistical software on a computer attached to an impedance meter or in some embodiments, even the impedance meter itself.

In another exemplary embodiment, the reference protein process may be intentionally altered to obtain a maximum or minimum allowable reference impedance value or limit to the range of allowable impedance values. For example, if a particular protein process requires the addition of ethanol to the protein mixture such that the resulting concentration of the protein mixture is 20% ethanol by volume, reference impedance values may be obtained for an otherwise identical reference protein process differing only in the production of a 15% or 25% by volume protein mixture. In this way, a practitioner would be able to compare a measured impedance value to a range of reference impedance values to determine if the alcohol content of the non-reference protein mixture is between 15% and 25%.

It will be understood that reference impedance values may be measured, determined or calculated at any number of different excitation frequencies. As discussed above, depending on the specific protein mixture, a frequency of an electrical signal propagated through a protein may be more strongly correlated to the real component of the impedance or the imaginary component of the impedance. Therefore, by determining the impedance at multiple frequencies, additional information may be obtained such that statistical software may be employed to establish the optimal frequency range for use, where the correlation between the real and/or imaginary components of the measured impedance and the characteristics of a particular protein mixture is the strongest. In some embodiments, the frequency, impedance value, protein mixture composition, protein mixture parameters and/or time may all be recorded in a database.

In still another embodiment, the real and/or imaginary impedance of a reference protein mixture may be measured at a single frequency and correlated to a particular parameter that modifies the solubility of a protein in a protein mixture undergoing a protein process, such as but not limited to: pH, conductivity, liquid/solid separation, water miscible organic precipitant concentration, protein aggregation, density, flow rate, viscosity, protein concentration, temperature and/or aging of proteins. For example, the real part of the impedance of a reference protein mixture having a known alcohol concentration may be measured at an excitation frequency of 0.02 kHz and a correlation of alcohol concentration to the impedance may be approximated for this frequency. The alcohol concentration of the mixture may then be adjusted and an approximated alcohol concentration may be determined using the correlation previously calculated. The accuracy of the correlation may then be determined by comparing the approximated alcohol concentration to the known or measured concentration.

Once a reference impedance value or range of reference impedance value is measured, ascertained, stored, known and/or is accessible, measured impedance values of protein mixtures may be compared thereto. In one embodiment, the impedance of a mixture may be determined at predetermined time intervals and each impedance measurement may be compared to a reference impedance value which was taken at that same time interval in a reference protein process. If the measured impedance value is within an acceptable deviation of the reference impedance value, the protein process is allowed to continue unmodified. However, if the measured impedance value is outside the range of acceptable impedance values, an adjustment may be made to the process or directly to the protein mixture. Alternatively or additionally, an operator may be notified of the deviation.

Exemplary Protein Processes

The present invention is not necessarily limited to any particular process for separating and/or purifying a protein from a biologic fluid. In fact, it is contemplated that any process for separating and/or purifying a protein from a biologic fluid may be controlled, adjusted, and/or monitored using the process control systems of the present invention, which utilizes IS as a means for measuring any suitable types of changes in the process. IS may be used to measure the compositions and monitor the progress of any step in any suitable protein process, such as, for example, a Cohn Fractionation Process, a Kistler Process, an Oncley Process or modifications thereof. Particularly suitable processes are described in U.S. Pat. No. 5,177,194, which is incorporated by reference herein in its entirety. In a preferred embodiment, the process control systems of the present invention may be used to control, adjust and/or monitor any step in a plasma fractionation process for the production of a purified fractionated protein product for administration to humans. Generally, the impedance of plasma mixtures may be measured throughout each fractionation and/or purification process step at one frequency or multiple frequencies, and the measured impedance values may be continuously compared to target reference impedance values or ranges of target reference impedance values to determine if the measured impedance values are within an acceptable tolerance (i.e. to determine if the process is proceeding correctly).

In some embodiments, a process step may only require a single variable of the plasma mixture to be changed (i.e. alcohol concentration) while other variables are held constant. In this particular embodiment, the impedance may be measured and compared to a reference impedance value or range of reference impedance values to determine the results of the process step (i.e. the resulting alcohol concentration in the plasma mixture). In other embodiments, a process step may require multiple variables to be adjusted (i.e. alcohol concentration, pH, and temperature), so the impedance may not be used to determine the actual value of a single parameter of the resulting plasma. Rather, the impedance may be measured to obtain a measured impedance value, and the measured impedance value may be compared to a target reference impedance value or target range of reference impedance values to determine if the process is proceeding according to the process plan. As described in detail above, if a measured impedance value is within an acceptable tolerance of a target reference impedance value, the process may proceed to a subsequent step either automatically or through the notification of a operator who may manually control the process. Additionally, if the measured impedance value deviates from a target impedance value or target range of reference impedance values by more than an acceptable tolerance, the process may be automatically adjusted, or an operator may be notified so that she may manually adjust the process or mixture utilized by the process.

Method for Monitoring and/or Controlling a Cohn Fractionation Process

In one exemplary embodiment, the plasma fractionation process may be a Cohn Fractionation Process or any variants thereof. For example, the process control systems of the present invention, such as, but not limited to, the exemplary embodiments shown in FIGS. 1 and 2 may be used to control, adjust and/or monitor the preparation of any protein plasma intermediate from a Cohn Fractionation Process, or any variants thereof. In a specific embodiment, IS may be used to monitor the production of cryoprecipitate, Fraction I, Fraction II+III, Fraction IV-1, Fraction IV-4, and/or Fraction V from a Cohn Fractionation Process or any variants, modifications and/or combinations thereof.

Figure 3:
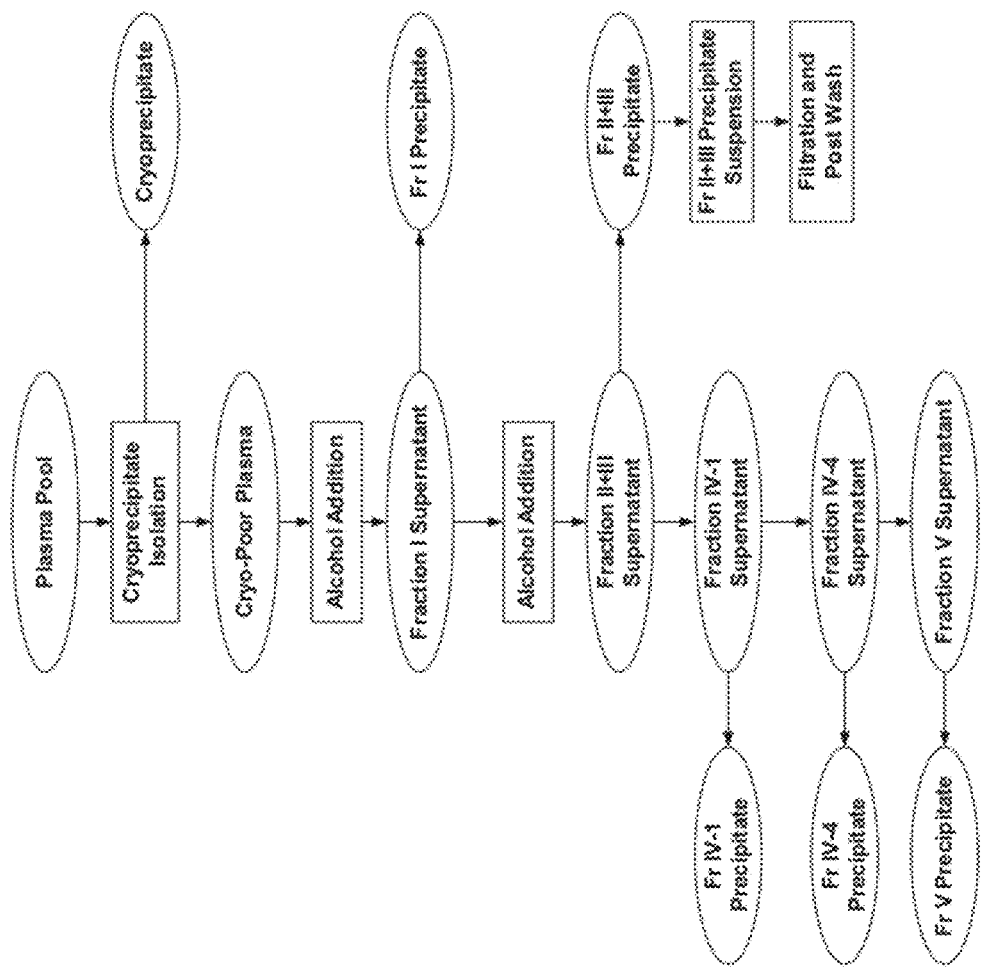
FIG. 3 shows a flow chart of an exemplary modified Cohn Fractionation Process.

Referring to FIG. 3, an exemplary variant of a Cohn Fractionation Process is shown, wherein fresh and/or thawed plasma may be combined to form a plasma pool. In the exemplary process shown, the fractionation begins with a cryoprecipitate isolation step that may be monitored and/or controlled using IS. Once the cryoprecipitate is removed from the plasma pool, the remaining protein mixture may be referred to as a cryo-poor plasma.

Fraction I

The next step in the exemplary process is to isolate Fraction I, which typically contains fibrinogen. In order to precipitate Fraction I from the cryo-poor plasma, the plasma mixture is stirred gently and brought to a temperature of from about 0° C. to about 2° C. The impedance of the plasma mixture may be continually measured and compared to a target reference impedance value or target range of reference impedance values to determine when the acceptable temperature is reached.

During stirring, a sufficient amount of an ethanol-water mixture having an ethanol concentration of, for example, about 53% may be added to the plasma mixture to bring the ethanol concentration of the resulting plasma solution to about 8% ethanol by volume. This step is shown in FIG. 3, and may be monitored and/or controlled using, for example, the exemplary systems shown in FIGS. 1 and 2. Specifically, the alcohol concentration of the plasma mixture may be determined or estimated by measuring the impedance of the mixture during the alcohol addition process step to obtain a measured impedance value, and the measured impedance value may be compared to a target reference impedance value or a range of target reference impedance values that were previously determined for this particular step in the process. In one embodiment, if the measured impedance value is within a target range of reference impedance values, the process may automatically trigger a subsequent step in the fractionation process.

The addition of a buffer, such as but not limited to sodium acetate-acetic acid, is next monitored and/or controlled using IS to increase the pH of the solution to from about 7.0 to about 7.4. If the buffer is added without changing other variables of the plasma mixture, the impedance may be measured and compared to a reference impedance value to determine the pH of the solution. However, if the buffer is added in solution with the ethanol-water mixture, the impedance of the plasma mixture may be measured and compared to a reference impedance value or range of reference impedance values which were previously determined based on change in both variables to determine if the process is proceeding according to the process plan.

During the addition of the ethanol-water mixture and/or buffer, the temperature of the plasma solution is lowered to from about −2° C. to about −3° C. by any means known in the art, for example, a water bath and/or cooling cables. Again, IS may be used to monitor and/or control this step by measuring the impedance and comparing the measured impedance values to reference impedance values determined under substantially similar process parameters and with substantially similar plasma mixtures. In one embodiment, the overall time for the addition of the alcohol and buffer is from about 1 hour to about 2 hours, and preferably about 90 minutes.

Once the above system parameters are obtained, Fraction I may be removed from the plasma solution by, for example, centrifugation at a temperature of from about −2° C. to about −3° C. This removal step may be monitored and/or controlled using IS, as the impedance may be correlated to the degree of protein aggregation and/or protein separation (see Example VIII and FIG. 6 below). By measuring the impedance during centrifugation, the process may automatically be stopped or a notification may be sent to an operator when the measured impedance value is within a target range of reference impedance values or is within an acceptable tolerance of a target reference impedance value.

Finally, once the Fraction I precipitate is obtained, it may be stored in an un-dried state at about −5° C., although loss of fibrinogen is expected after a few months. Such loss may be monitored using IS, as protein aging may be correlated to the impedance of the Fraction I precipitate. Therefore, the impedance of the stored Fraction I precipitate may be measured, and the measured impedance value may be compared to a reference impedance value or range of reference impedance values to determine the loss of fibrinogen.

Cohn Fraction II+III

The next step in the exemplary Cohn Fractionation process will produce Cohn Fraction II+III, which contains about 30% to about 85% IgG polyclonal antibodies, about 5% to about 30% IgA, about 1% to about 25% IgM, and trace amounts of other components such as, for example, clotting factors II, VII, IX, X and alpha and beta globulins. It is contemplated that IS may be used to monitor and/or control multiple variables and/or sub-steps in this process.

After removal of Cohn Fraction I from the plasma solution, the resulting supernatant is cooled to about −5° C., and the pH is adjusted to from about 6.7 to about 6.9 by the addition of a buffer. The buffer may be any buffer known in the art, but may preferably be the same buffer as used in the process for removing Fraction I. Additionally, a cold ethanol solution having a concentration of about 53% ethanol is added to the supernatant such that the resulting concentration of alcohol in the plasma solution is about 25% alcohol by volume. In one embodiment, the total time required for the addition of the alcohol and buffer is about 5 hours. As described above with respect to Fraction I, IS may be used to monitor and/or control each of these process steps, whether they occur sequentially or in combination. Moreover, IS may be used in a similar manner as that described above with respect to Fraction I to monitor and/or control the precipitation of Fraction II+III from the resulting suspension using such methods as but not limited to centrifugation and collection.

Once removed, Fraction II+III may be stored in an undried form for about a year without measurable degradation of the protein. It is contemplated that the impedance of undried Fraction II+III may be correlated to the protein degradation as described above, and substantial changes in the undried form may be prevented by notification of an operator through repeated and/or continuous measurement and comparison of the impedance, preferably in real-time or near real-time.

Fraction IV-1

Similarly, IS may be used to monitor and/or control multiple steps in the precipitation of Cohn Fraction IV-1 from the supernatant resulting from the removal of Fraction II+III. In this process, water having a temperature of about 0° C. may first be added to the supernatant to decrease the ethanol concentration of the solution to about 18% ethanol by volume. A buffer such as the buffer used to obtain Fraction I and/or Fraction II+III may be added to the plasma solution such that the pH is lowered to from about 5.0 to about 5.4. In one embodiment, the temperature is held constant at about −5° C. throughout the process. IS may be used to monitor and/or control, in a similar manner as that described above with respect to Fraction I, the alcohol concentration and/or the pH of the plasma mixture whether these variables are changed at the same time or are changed in separate steps.

After addition of alcohol and buffer is complete, the plasma mixture is stirred for about one hour and allowed to stand for from about 6 to about 8 hours to allow for the completion of the precipitate. Because impedance may be correlated to such variables as protein aggregation, protein aging, and protein concentration, impedance measurements of the stirred plasma mixture may be used to efficiently determine the completeness of the precipitate, saving valuable time. The impedance of a Fraction IV-1 suspension may be monitored in real-time or near-real time and compared to a target reference range of impedance values and/or a target impedance value to determine the completeness of the precipitate. If the measured impedance is within the target reference range of impedance values, the process may be allowed to continue onto the next step. In another embodiment, once the measured impedance is within the target reference range of impedance values, an operator may be alerted.

Fraction IV-1 may be removed from the plasma solution by, for example, centrifugation and such removal may be monitored and/or controlled using IS, as described above with respect to Fraction I.

Fraction IV-4

Cohn Fraction IV-4 consists primarily of alpha and beta globulins and albumin. In one exemplary embodiment, IS may be used to monitor and/or control the various process steps in the production of Fraction IV-4 from a plasma mixture. Once Fraction IV-1 is removed from the plasma mixture, a buffer may be added to the mixture over a period of about 90 minutes in order to increase the pH to about 5.8. Following buffer addition, an ethanol solution, such as a 95% ethanol solution, may be added to the solution to increase the ethanol concentration to about 40% by volume. The temperature may be held constant at about −5° C. throughout the process. As described above with respect to Fraction I, IS may be used to monitor and/or control the pH, alcohol concentration and/or temperature of the plasma mixture whether changed independently or in combination. Fraction IV-4 may be removed from the solution by, for example, centrifugation and such removal may be monitored and/or controlled using IS in a similar manner as described above with respect to Fraction I.

Fraction V

Cohn Fraction V contains the bulk of the albumin present in the starting plasma pool and generally contains less than 3% of alpha-globulin and less than 0.5% of beta-globulin. It is contemplated that the IS methods described above with respect to Fraction I may be used to monitor and/or control the purification of Fraction V from a plasma solution such as the supernatant remaining after removal of Fraction IV-4, which contains mostly albumin with a small amount of suspended material. This suspended material may be removed by, for example, filtration to produce a highly clarified fraction. In one embodiment, 0.5% washed standard super-cel is added to the plasma solution and the resulting suspension is filtered through a filter at about −5° C. The impedance of the protein mixture may be measured throughout the filtration step, and compared to reference impedance values or a range of reference impedance values.

After filtration, a post wash step may be performed by, for example, using a 40% ethanol solution containing about 0.1 mole of sodium chloride per liter of solution. The post wash step may be monitored and/or controlled using IS, as the impedance may be correlated to protein concentration and protein aggregation. Therefore, impedance of the plasma mixture may be measured throughout the post wash process to determine when the measured impedance is within a target range of reference impedance values, and, thus, determine when the post wash is complete.

After clarification, all filtrates and washings are combined into a solution, and the pH of the solution is lowered to about 4.8 by the addition of a buffer such as sodium acetate-acetic acid. The temperature is held constant at from about −5° C. to about −6° C. during the buffer addition, and said buffer addition is performed over the course of about 2 hours. The solution is allowed to stand for at least 3 hours without stirring, and Fraction V paste may be precipitated out by, for example, centrifugation or filtration. Again, IS may be used to monitor and/or control the addition of buffers, the temperature change and/or degree of separation of Fraction V as described above.

In one embodiment, the Fraction V paste may be further purified to remove electrolyte content for use in certain clinical applications and such purification may be monitored and/or controlled using IS. In this embodiment, an ethanol solution and buffer as described above may be added over the course of about 2 hours to the Fraction V paste to prepare a solution containing about 3% protein, 10% ethanol, 0.01 M salt, and a pH of from about 4.5 to about 4.7. Generally, the temperature is reduced during the addition to from about −2° C. to about −3° C. The resulting turbid solution is stirred gently, but thoroughly, for about two additional hours.

Figure 17:
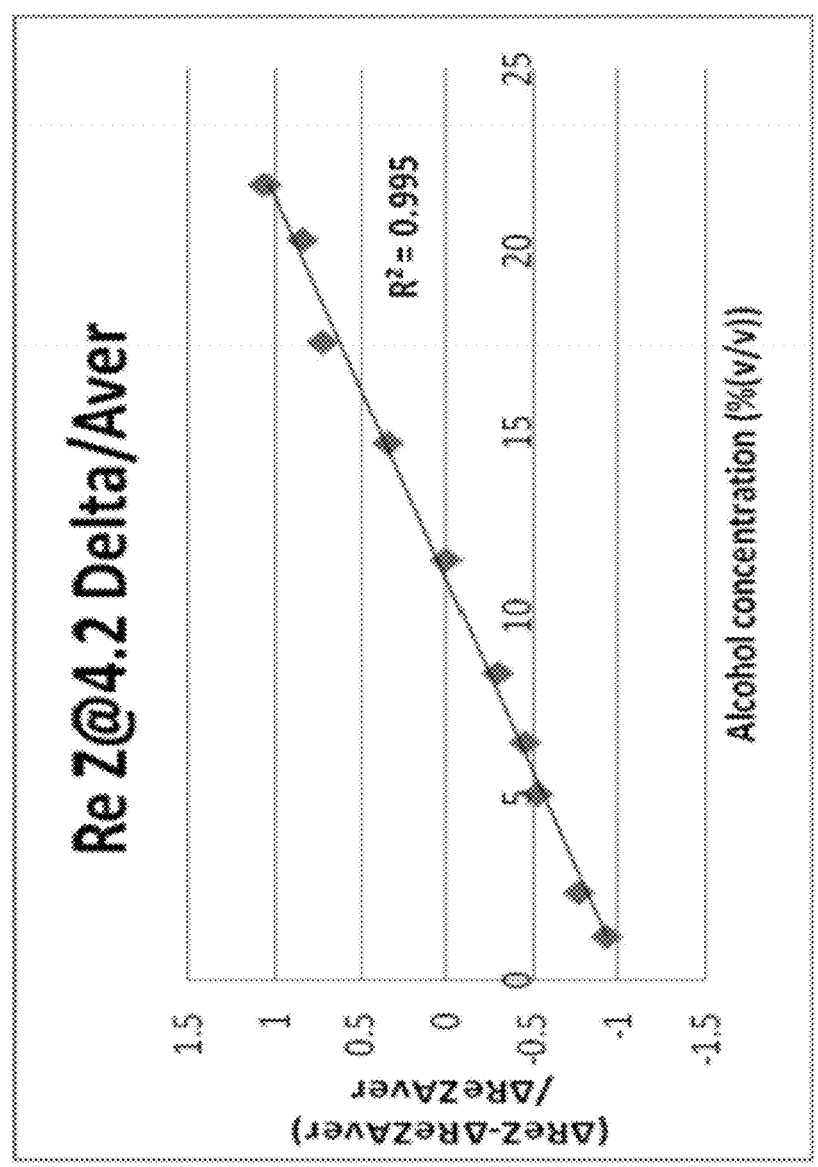
FIG. 17 shows an exemplary graphical representation of ΔRe Z Centered vs. Average for a 5% albumin solution undergoing an alcohol addition process.

In yet another embodiment, the resulting solution from the above embodiment may be further filtered by, for example, suspending about 0.25% of standard super-cel in the solution and filtering through a filter pad at a temperature of about −2° C. If any albumin is occluded by the filter cake, it may be washed out with a small volume of solution comprising, for example, about 10% ethanol at −2° C. IS may be used to monitor and/or control the filtration and post-wash process steps, and although described herein with respect to the purification of Fraction V, it will be appreciated that any of the fractionated plasma intermediates may be filtrated and/or washed, and such filtration and/or washing may be monitored and/or controlled via the IS techniques described herein. For example, and as shown in FIG. 17, IS may be used to monitor and/or control the post-wash and/or filtration of Fraction II+III.

In another embodiment, if the level of unstable impurities in solution is determined to be higher than is desired or allowed either by IS methods or otherwise, the ethanol concentration of the wash may be raised from about 10% to about 15% and the temperature may be lowered to from about −2° C. to about −5° C. Again, IS may be used to monitor and/or control this process step as described above.

Once filtered, albumin may be precipitated from the filtrate by raising the ethanol concentration of the solution to about 40% through the addition of, for example, a 95% ethanol solution. During ethanol addition, the pH may be raised to from about 5.0 to about 5.4 by the addition of, for example, sodium bicarbonate, while the temperature is lowered to from about −5° C. to about −6° C. This process may take about two hours to complete, and once the desired parameters are obtained (as measured and/or determined using impedance measurements), albumin may be removed by centrifugation or filtration. The albumin may be dried from the frozen state at as low a temperature as is practical.

It will be appreciated that the process control systems of the present invention may be used to control, adjust and/or monitor any step in many variations of the above described Cohn Fractionation Process. For example, in one embodiment, the process control systems of the present invention, such as, but not limited to, the exemplary embodiments shown in FIGS. 1 and 2, may be used to control, adjust and/or monitor the preparation of any intermediate compositions from a Kistler Process, or any variants thereof. In a specific embodiment, impedance spectroscopy may be used to monitor and/or control each step in the production of Kistler Precipitate A, Kistler Precipitate B, Kistler Precipitate IV, Kistler Precipitate C, Kistler Precipitate D from a Kislter Process or any variations, combinations or modifications thereof.

In another exemplary embodiment, the process control systems of the present invention, such as, but not limited to, the exemplary embodiments shown in FIGS. 1 and 2, which use impedance measurements to control and/or monitor protein processes, may be used to control, adjust and/or monitor the preparation of any intermediate compositions from a Tescher Process, or any variants thereof. The impedance may be measured and compared to reference impedance values or ranges of reference impedance values at any process step in the Tescher Process, such as but not limited to: cryoseparation, adsorption of blood coagulation factors and antithrombin, modified ethanol fractionation, S/D treatment, cation-exchange chromatography, anion-exchange chromatography, ultra-/diafiltration, nanofiltration, concentration formula filling, lyophilization, and/or incubation. In a specific embodiment, impedance spectroscopy may be used to monitor and/or control each step in the production of Tescher Precipitate G. Because the instantly claimed systems and methods are not limited to a particular protein process, it will be appreciated that any variations, combinations, or modifications to the Tescher Process may be monitored and/or controlled using IS.

Method for Monitoring and/or Controlling a Oncley Fractionation Process

In another exemplary process, the process control systems of the present invention may be used to control, adjust and/or monitor any step in the Oncley Fractionation Process or any variants thereof. In a specific embodiment, IS may be used to monitor and/or control: alcohol concentration, ionic strength, pH, temperature, purification, centrifugation, protein separation, protein agglomeration, protein concentration and/or protein aging each step of the production of Fraction II+IIIw, Fraction II, and Fraction III.

Fraction II+IIIw

In one embodiment, the impedance monitoring and control techniques of the instant invention are employed in a Fraction II+IIIw production process. First, a Fraction II+III precipitate may be suspended in cold water in a volume ratio of about 1:5, about 1:10, about 1:15, or about 1:20 Fraction II+III to water. Such volume ratios may be determined using IS, as described above, as these values may correspond to protein concentration. The ionic strength of the resulting plasma mixture may be monitored and/or adjusted using IS as described above to from about 0.003 m to about 0.005 m by the addition of, for example, a sodium phosphate solution. An ethanol solution may also be added to the plasma mixture such that the resulting mixture has an alcohol concentration of from about 20% to about 25% alcohol by volume. Such alcohol addition may be controlled and/or monitored using IS in a similar manner as described above relating to an exemplary Cohn Fractionation Process. Generally, the temperature of the solution may be lowered to about −5° C. during the process, and the pH may be maintained or adjusted to from about 7.2 to about 7.6 by, for example, using an acetate buffer or dilute sodium hydroxide. These process steps may be monitored and/or controlled using IS whether they are completed in combination or independently. Once the necessary parameters are obtained, the Fraction II+IIIw precipitate may be recovered by any means known in the art, including but not limited to centrifugation and/or filtration at about −5° C.

Fractions II and III

The impedance measurement, monitoring and control techniques of the instant application are contemplated as being useful in any number of processes for the storing and/or separation of fractionated plasma intermediates, such as but not limited to Fraction II+IIIw, into individual components and subcomponents. In one exemplary embodiment, a Fraction II+IIIw precipitate may be dissolved in a sufficient amount of water at a temperature of about −5° C. to result in a solution having 1% protein concentration. Both the temperature change and protein concentration may be determined and/or controlled using IS in a similar manner as described above relating to an exemplary Cohn Fractionation Process. The pH of the solution may be maintained or adjusted to about 7.2, and cold ethanol may be added such that the solution has a resulting alcohol concentration of from about 20% to about 25% alcohol by volume, and such process steps may be monitored and/or controlled using IS as described above. In one embodiment, the solution is allowed to stand at about −5° C. for an amount of time from about 2 to about 24 hours. As described above, IS may be used to monitor and/or control the separation of Fraction II, which contains about 95% to about 99% IgG polyclonal antibodies, at least 0.01% to about 2% IgM and trace amounts of salt by, for example, centrifugation of the plasma mixture.

Once Fraction II is removed from the plasma mixture, IS may be used to control and/or monitor the precipitation of Fraction III out of the supernatant by adjusting the pH to about 5.7 and adding alcohol to reach a final concentration of about 25% alcohol by volume. The mixture may then be allowed to stand without further modification for an amount of time of from about 2 to about 24 hours, depending on the degree of separation, which may be monitored and/or controlled using IS. Fraction III, which contains at least about 25% IgG polyclonal antibodies, at least about 5% to about 30% IgA and about 1% to about 25% IgM, together with trace amounts of clotting factors II, VII, IX, alpha and beta globins and lipids, may then be removed by, for example, centrifugation monitored and/or controlled by IS. Importantly, IS may be employed in each step in the production of Fraction III, whether each step is completed independently or in combination with other steps, as long as a reference impedance value or range of reference impedance values is previously obtained.

Method for Monitoring and/or Controlling an Immune Globulin Purification Process In another embodiment, the impedance systems and methods described herein may be used to monitor and/or control the separation of immune globulins from fractionated plasma intermediates, such as but not limited to Cohn Fraction I, Cohn Fraction II, Cohn Fraction III, Cohn Fraction II+III, and/or Cohn Fraction I+II+III. In a first step, a fractionated plasma intermediate is suspended in water at a substantially non-denaturing temperature and acidic pH. As used herein, "substantially non-denaturing" means that the condition to which the term refers does not cause substantial irreversible loss of biological activity of the immune serum globulins. Such temperatures and pH levels may be determined, monitored, adjusted and/or controlled using IS in a similar manner as described above relating to an exemplary Cohn Fractionation Process.

The crude plasma protein fraction may be suspended in cold water at volumes from about 5 to about 10 times the weight of the fraction. The water is preferably maintained at a cold temperature which prevents substantial denaturing of the immune serum globulin proteins. Temperatures of from about 0° C. to about 10° C., preferably from about 1° C. to about 3° C. are typically employed. Moreover, the suspension may be optionally acidified with a non-denaturing acid and the pH of the suspension may be maintained from about 4.5 to about 5.5, preferably from about 5.0 to about 5.2. Similar to that described above for an exemplary Cohn Fractionation Process, the temperatures and pH values of this exemplary immunoglobulin purification process may also be monitored and/or controlled using IS.

By adding a protein precipitant, non-serum globulin proteins, lipids, and some viruses may be precipitated from the suspension without causing substantial precipitation of immune serum globulins. Substantially non-denaturing, water soluble protein precipitants are well-known in the protein purification arts, and suitable protein precipitants include, for example, various molecular weight forms of polyethylene glycol, ammonium sulfate, polyvinylpyrrolidone and pluronics. The protein precipitant may be added to the crude plasma protein suspension as a solid, or an aqueous concentrate derived from commercially available solid powder or flakes. The actual amount of protein precipitant used will vary, depending upon the particular precipitant employed, the temperature, pH and protein concentration in suspension, however, IS may be used to monitor and/or control the addition based on these parameters. Generally, the precipitation is maintained at a low temperature (e.g. less than about 10° C.) and allowed to proceed until equilibrium is reached (e.g. generally for about one hour or more).

Following precipitation, an immune globulin-containing liquid is recovered from the solids-liquid mixture resulting from the precipitation. Recovery of the clarified liquid can be accomplished by conventional solids-liquid separation techniques, such as centrifugation and filtration, and such recovery may be monitored using IS to determine the completeness (degree of protein separation) and/or process parameters in a similar manner as described above relating to an exemplary Cohn Fractionation Processes.

Infectious viruses that may still be present in the crude plasma protein fraction can be inactivated by adding a virucidal amount of a virus-inactivating agent to the clarified immune serum globulin-contain liquid. Generally, the impedance techniques of the present invention are thought to be useful in monitoring the addition of virus-inactivating agents such as: detergents (e.g. oxyethylated alkylphenols, polyethylated derivates of a partial ester of a $C_{12-22}$ fatty acid and a hexatol anhydride, lower alkyl ester of phosphoric acid, and combinations thereof). In general, the virus-inactivating step is conducted under virus-inactivating conditions. These conditions include temperatures of from about 10° C. to about 30° C., preferably from about 18° C. to about 22° C. Moreover, an incubation time of about one hour may be sufficient.

In another embodiment, once virus inactivation is complete, the immune globulin-containing solution may be contacted with a cation exchange resin to remove the virus-inactivating agent and other non-serum globulin contaminants. As an example, the solution may be passed over a column packed with a cation exchange resin, such as carboxymethyl agarose. The column may be equilibrated with a buffer, such as an acetate, capable of converting the resin to the salt form. The resulting mixture may be monitored and/or controlled using IS, such that the impedance of the solution may be measured and compared to reference impedance values from a substantially similar process using substantially similar components.

Prior to loading the immune globulin-containing solution onto the column, the salt concentration of the solution may be monitored and adjusted using IS, to an amount substantially equivalent to the salt concentration of the equilibration buffer. Generally, after the solution is loaded onto a column, the column is washed sequentially with the same buffer used for equilibration and the washing process may also be monitored and/or controlled using IS.

The immune globulins may then be eluted from the cation exchange resin with a substantially non-denaturing buffer having a pH and ionic strength sufficient to cause substantial elution of the immune globulins. In a similar manner as described above relating to a Cohn Fractionation Process, IS may be used to ascertain such parameters as: the pH (preferably from about 7.0 to about 8.5), salt concentration, polyethylene glycol and/or glycine concentration. Once the immune globulins are eluted, the elute may be concentrated and filtered, and the process may be repeated as desired or required. In one embodiment, the process may be repeated if the immune globulin concentration, as determined using IS, is below a desired or required value. It is contemplated that de minimis changes to other components of a solution that do not result in a measurable or significant change to the impedance of the solution will not materially or significantly effect the overall correlation of impedance values to any particular characteristic of the solution including: ionic concentration, protein concentration, water miscible organic precipitant concentration, pH, temperature and/or any combination thereof.

The foregoing description and drawings are illustrative of the invention, but are not to be construed as limiting the invention. Numerous specific details are described to provide a thorough understanding of various embodiments of the present invention, however, in certain instances, well-known or conventional details are not described in order to provide a concise discussion of embodiments of the present inventions.

EXAMPLES

Example I

In one exemplary embodiment, ranges of reference impedance values were measured at a number of different frequencies and pH values for a albumin solution. A predetermined, measured amount of basic solution was added to the albumin solution while all other physical and chemical properties were held constant. Multiple impedance measurements were taken at a number of frequencies and stored in a general purpose computer. These steps were repeated for pH levels of 3.2, 4.2 and 7.4. The data shows that the complex impedance of a 5% by volume albumin solution may depend from and may be correlated to pH.

Figure 4:
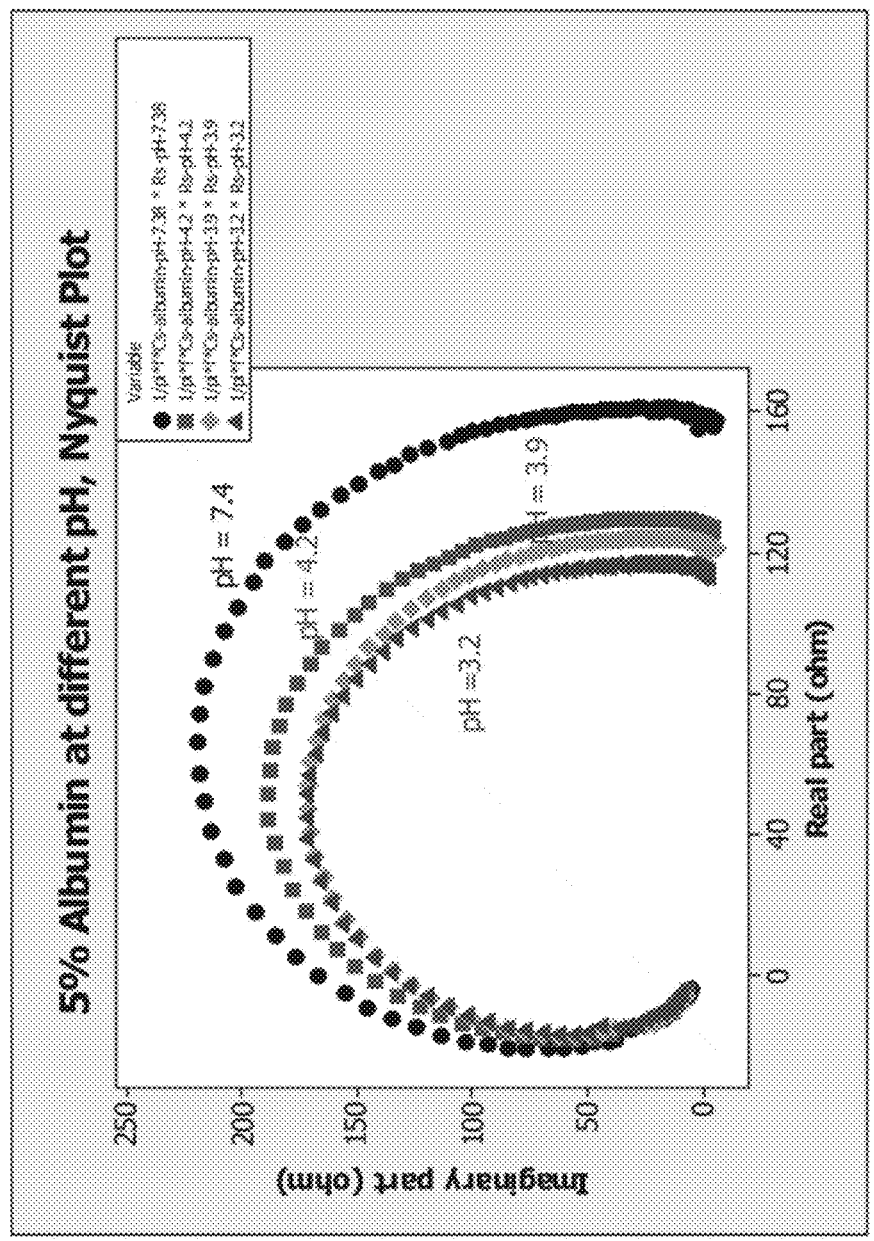
FIG. 4 illustrates an exemplary Nyquist plot showing that the impedance of an albumin solution may be correlated to the pH of the solution.

Referring to FIG. 4, an exemplary Nyquist Plot is shown wherein the real part of the impedance of the 5% by volume albumin solution is plotted against the imaginary part of the impedance of the same solution at multiple frequencies ranging from 2 KHz to 1.7 MHz and at multiple pH levels. Thus, the effect of pH on impedance is clearly seen through visual inspection of the exemplary Nyquist Plot, and impedance may therefore be correlated to pH.

In an exemplary embodiment, the Nyquist Plot of FIG. 4 may be used to extrapolate the pH level of a sample solution having otherwise the same or similar composition, based on impedance measurements of such a solution at frequencies ranging from 2 KHz to 1.7 MHz. It is contemplated that impedance values of any solution may be correlated to the pH of the solution using a Nyquist plot similar to that shown in FIG. 4.

The correlation of the real and imaginary parts of the impedance (Re Z and Im Z, respectively) of the albumin solution to pH concentration of that solution was determined. In order to resolve optimal frequency range(s) to be implemented, statistical software (Minitab 15.1.1.0) was employed and the following linear regression equations were determined:

$$ReZ(f)=A(f) \times pH+B(f) \quad \text{Equation 5}$$

$$ImZ(f)=A'(f) \times pH+B'(f) \quad \text{Equation 6}$$

Table I below presents the results of the impedance measurements indicating the strong correlation ($R^2>95\%$) between Re Z (at frequencies below 50 kHz), and Im Z (at frequencies above 50 KHz) and pH. The coefficients A, B, A', B' as well as the corresponding Coefficients of Determination ($R^2$) at different frequencies were solved and are presented in Table I. The optimal frequency ranges of 6.3, 15.9 and 50.2 for Re Z and 159.0 and 502.4 for Im Z (shown in bold) were defined as those where the $R^2 \geq 95\%$ for either Re Z or Im Z.

TABLE 1

| f (kHz) | Log(f) | Re Z | | | Im Z | | |
|---|---|---|---|---|---|---|---|
| | | A | B | $R^2$ | A' | B' | $R^2$ |
| 6.3 | 3.8 | 10.2 | 84.2 | 99.6 | 0.60 | −0.89 | 94.7 |
| 15.9 | 4.2 | 10.4 | 84.3 | 99.6 | 1.98 | 3.23 | 94.9 |
| 50.2 | 4.7 | 9.9 | 85.7 | 99.6 | 7.2 | 14.8 | 95.2 |
| 159.0 | 5.2 | 1.82 | 91.3 | 78.3 | 17.2 | 75.8 | 94.0 |
| 502.4 | 5.7 | −3.15 | 3.88 | 93.2 | −3.76 | 130.8 | 96.9 |
| 843.0 | 5.9 | −0.5 | −14.8 | 93.4 | −2.5 | 56.4 | 83.9 |
| 1589.0 | 6.2 | 0.5 | −8.8 | 66.9 | −0.9 | 12.2 | 91.2 |

Example II

The complex impedance of a 5% by volume albumin solution was shown to be dependent upon sodium concentration. Ranges of reference impedance values were measured at a number of different frequencies and sodium concentrations. A predetermined, measured amount of sodium was added to the albumin solution while all other physical and chemical properties were held constant, and multiple impedance measurements were taken at a different frequencies and stored in a general purpose computer. These steps were completed for sodium concentrations of 0% by weight, 3.3% by weight, 9.5%, by weight, and 15% by weight.

Figure 5:
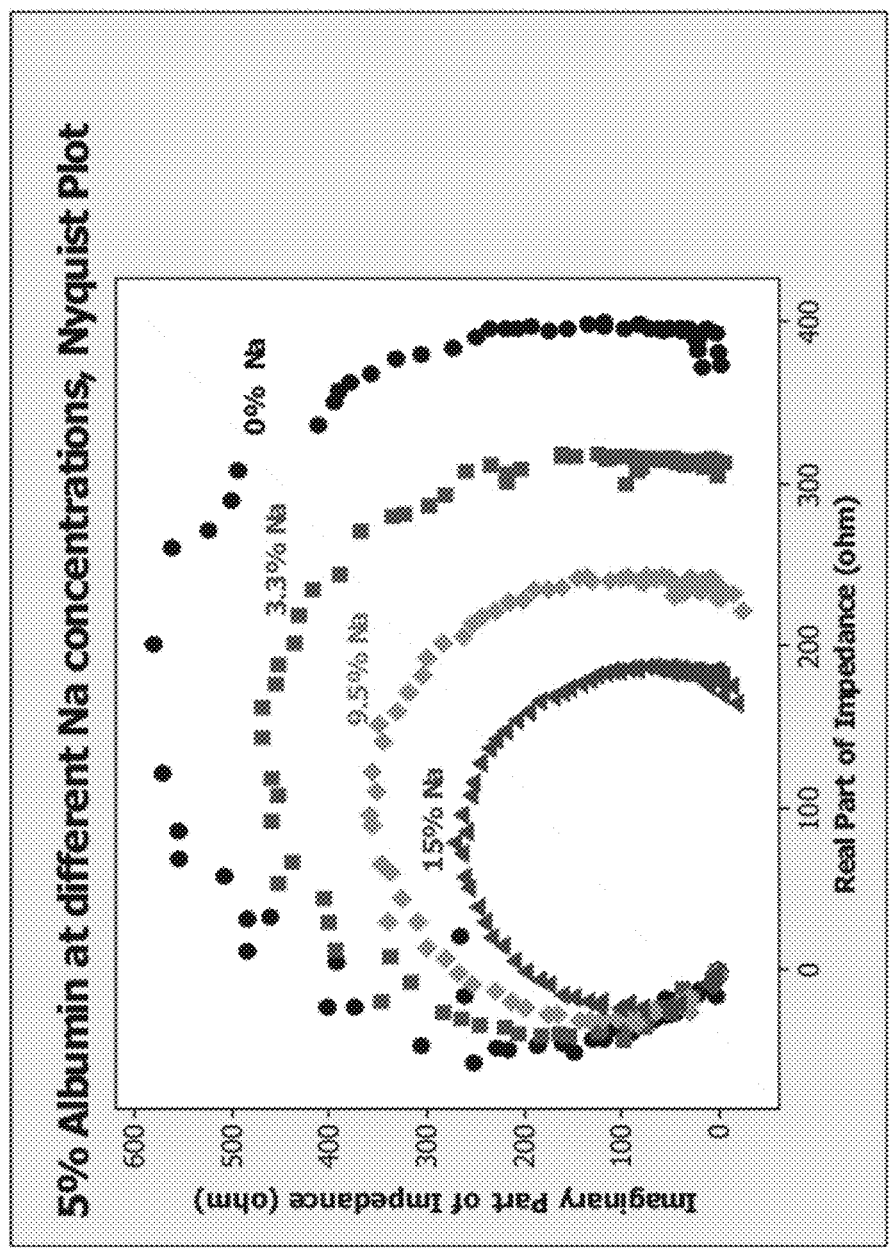
FIG. 5 illustrates an exemplary Nyquist plot showing that the impedance of an albumin solution may be correlated to the sodium concentration of the solution.

Referring to FIG. 5, an exemplary Nyquist Plot is shown wherein the real part of the impedance of the 5% by volume albumin solution is plotted against the imaginary part of the impedance of the same solution at multiple frequencies ranging from about 1 KHz to about 2 MHz and at multiple sodium concentration levels. As shown, impedance values were determined at multiple frequencies for sodium levels of 0% by weight, 3.3% by weight, 9.5%, by weight, and 15% by weight. Thus, the effect of sodium concentration on impedance of the albumin solution is seen through visual inspection of the exemplary Nyquist Plot and impedance may therefore be correlated to sodium concentration.

In an exemplary embodiment, the Nyquist Plot of FIG. 5 may be used to extrapolate the sodium concentration of a sample solution having otherwise the same or similar composition, based on impedance measurements of such a solution at frequencies ranging from about 1 KHz to about 2 MHz. It is contemplated that impedance values of any solution may be correlated to the sodium concentration of the solution using a Nyquist plot similar to that shown in FIG. 5.

Example III

The complex impedance of a Fraction II+III suspension containing 20% by volume alcohol was shown to decrease upon centrifugation. In one exemplary embodiment, ranges of reference impedance values were measured at a number of different frequencies before and after centrifugation. Centrifugation was performed for 30 minutes at 5000 G of force at a temperature of −3° C.

Figure 6:
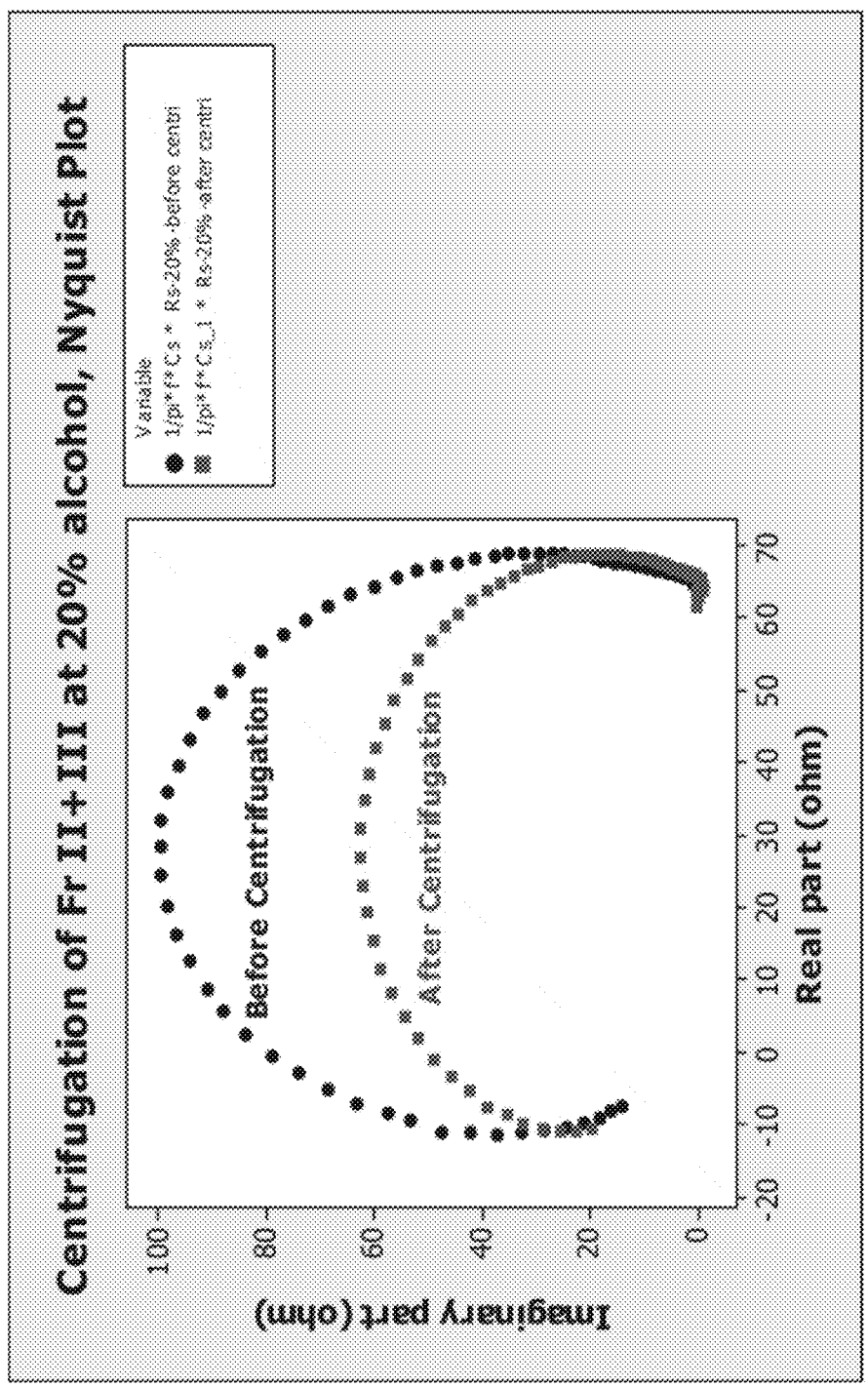
FIG. 6 illustrates an exemplary Nyquist plot showing that the impedance of a Fraction II+III paste suspended at 20% alcohol concentration may be correlated to the degree of protein separation in the solution.

The results are shown in the exemplary Nyquist Plot of FIG. 6, wherein the real part of the impedance of the solution is plotted against the imaginary part of the impedance of the same solution at multiple frequencies ranging from about 1 KHz to about 2 MHz. As shown, the impedance of the Fraction II+III suspension at 20% alcohol was affected by the centrifugation process. Thus, impedance may be correlated to degree of liquid-solid separation.

In an exemplary embodiment, the Nyquist Plot of FIG. 6 may be used to extrapolate the degree of liquid-solid separation of a sample solution, having otherwise the same or similar composition, based on impedance measurements of such a solution at frequencies ranging from about 1 KHz to about 2 MHz. It is contemplated that impedance values of any protein suspension may be correlated to the degree of liquid-solid separation using a Nyquist plot similar to that shown in FIG. 6.

Example IV

The complex impedance of a cryo-poor plasma mixture was determined to be dependent on alcohol concentration. Ranges of reference impedance values were measured at a number of different frequencies and alcohol concentrations. A predetermined, measured amount of alcohol was added to the cryo-poor mixture while all other physical and chemical properties were held constant, and multiple impedance measurements were taken at a different frequencies and stored in a general purpose computer. These steps were completed for alcohol concentrations of 0% by volume, 8% by volume, and 20% by volume. Additionally, in a second run, these steps were completed for additional alcohol concentrations of 11% by volume, 14% by volume, and 17% by volume.

Figure 7:
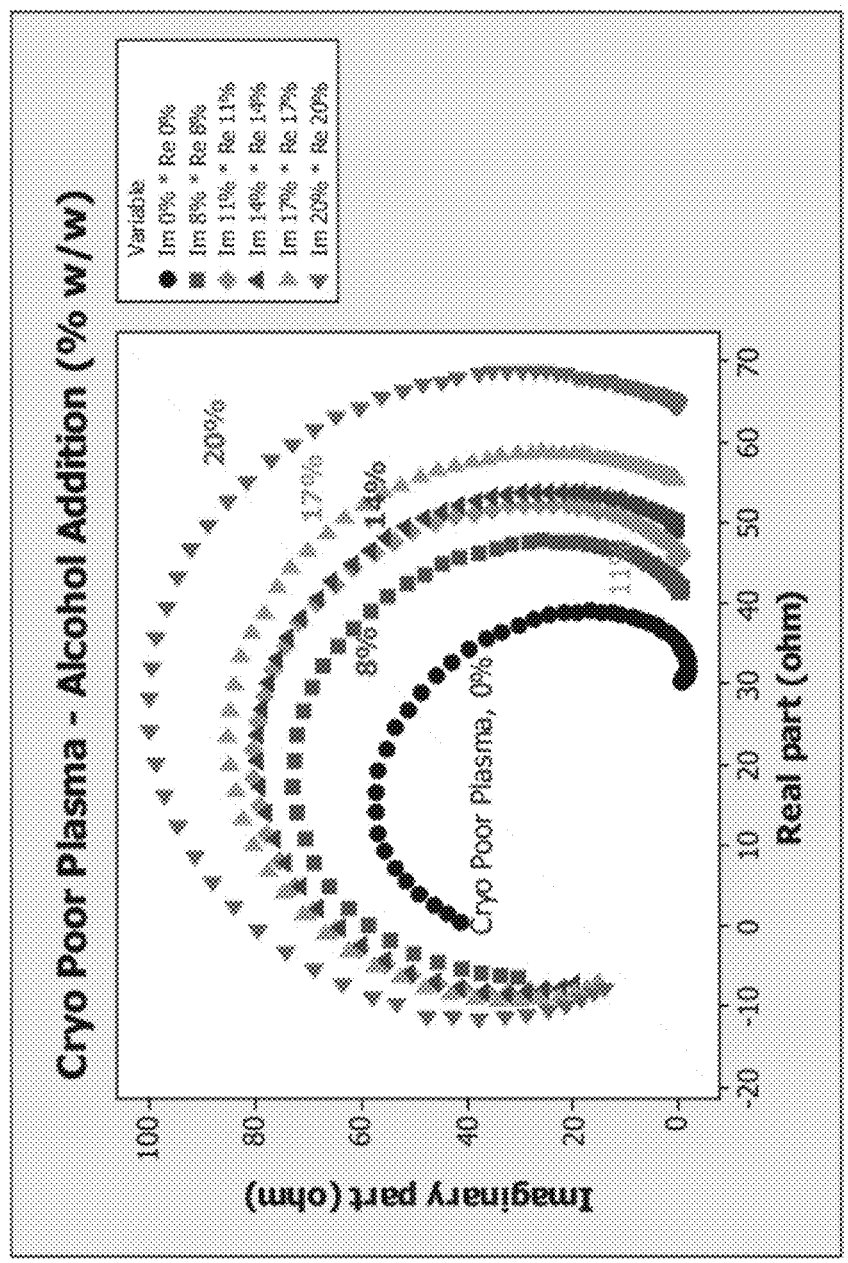
FIG. 7 illustrates an exemplary Nyquist plot showing that the impedance of a cryo-poor plasma solution may be correlated to alcohol concentration in the plasma.

Referring to FIG. 7, an exemplary Nyquist Plots is shown wherein the real part of the impedance of a cryo-poor plasma mixture is plotted against the imaginary part of the impedance of the same solution at multiple frequencies ranging from about 1 KHz to about 2 MHz and at multiple alcohol concentration levels. The impedance values were determined at multiple frequencies for alcohol concentration levels of 0%, 8%, 11%, 14%, 17% and 20% by volume. Thus, the effect of alcohol concentration on impedance of the cryo-poor plasma mixture is clearly seen through visual inspection of the exemplary Nyquist Plot and impedance may therefore be correlated to alcohol concentration of cryo-poor plasma mixtures.

In an exemplary embodiment, the Nyquist Plots of FIG. 7 may be used to extrapolate alcohol concentration in a sample cryo-poor plasma solution based on impedance measurements of such a solution at frequencies ranging from about 1 KHz to about 2 MHz, without knowing the alcohol concentration.

Example V

Figure 8:
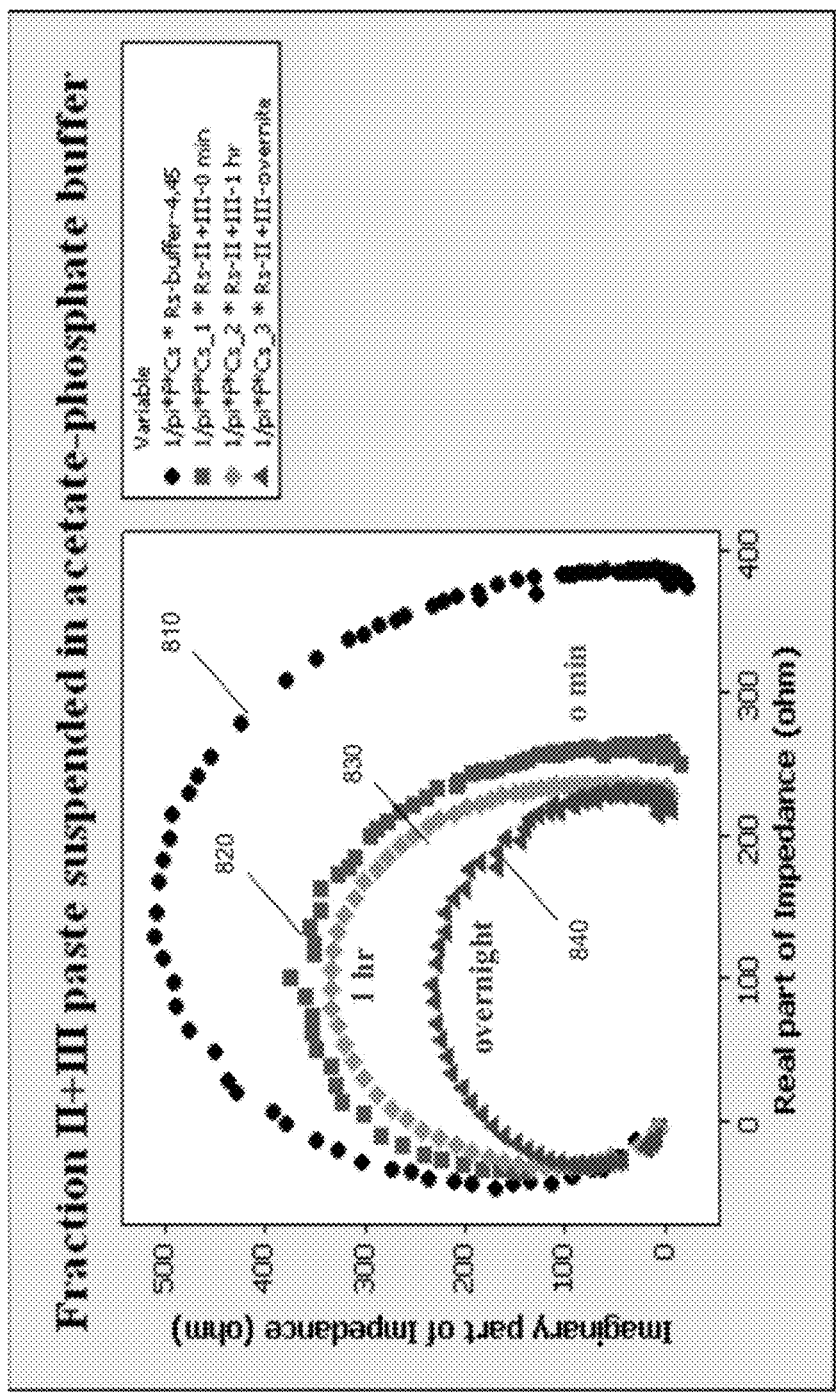
FIG. 8 illustrates an exemplary Nyquist plot showing that the impedance of a Fraction II+III paste suspended in acetate-phosphate buffer may be correlated to the aging of the suspension.

The complex impedance of a Fraction II+III paste suspended in acetate-phosphate buffer was determined to be dependent on protein aging. Ranges of reference impedance values were measured at a number of different frequencies and times of aging of the suspension. Multiple impedance measurements were taken at different frequencies and at each predetermined time interval, and these measurements were stored in a general purpose computer. The impedance was measured at time intervals ranging from about 0 minutes to multiple hours ("i.e. "over night."). As can be seen in FIG. 8, as a protein solution ages, the impedance of such a solution may change over time.

Referring to FIG. 8, an exemplary Nyquist Plot is shown wherein the real part of the impedance of the suspension is plotted against the imaginary part of the impedance of the same suspension at multiple frequencies ranging from about 1 KHz to about 2 MHz and at multiple times ranging from 0 minutes to multiple hours (i.e., "over night"). As shown, impedance values were determined at multiple frequencies 810 for the acetate-phosphate buffer before a Fraction II+III paste was added. Impedance values were determined at multiple frequencies at the time of addition of the Fraction II+III paste 820, 1 hour after addition 830, and multiple hours after addition 840. Thus, the effect of aging on the Fraction II+III paste suspended in acetate-phosphate buffer is clearly seen through visual inspection of the exemplary Nyquist Plot and impedance may be correlated to such aging.

In an exemplary embodiment, the Nyquist Plot of FIG. 8 may be used to extrapolate the age of a protein mixture based on impedance measurements of such a solution at frequencies ranging from about 1 KHz to about 2 MHz. It is contemplated that impedance values of any protein solution may be correlated to its age using a Nyquist plot similar to that shown in FIG. 8.

Example VI

In an exemplary embodiment, IS was used to monitor the concentration of Human Immunoglobulin G (IgG) in a biologic fluid. The correlation of the real and imaginary parts of the impedance (Re Z and Im Z, respectively) of a biologic fluid to IgG concentration in the biologic fluid was determined by measuring the impedance of the biologic fluid at certain frequencies during a suspension process. About 1.6 L of Fraction II+III paste was suspended in an extraction buffer composition. The mixture was contained in a 10 liter jacketed process tank and the temperature was held constant using a water bath.

Figure 9:
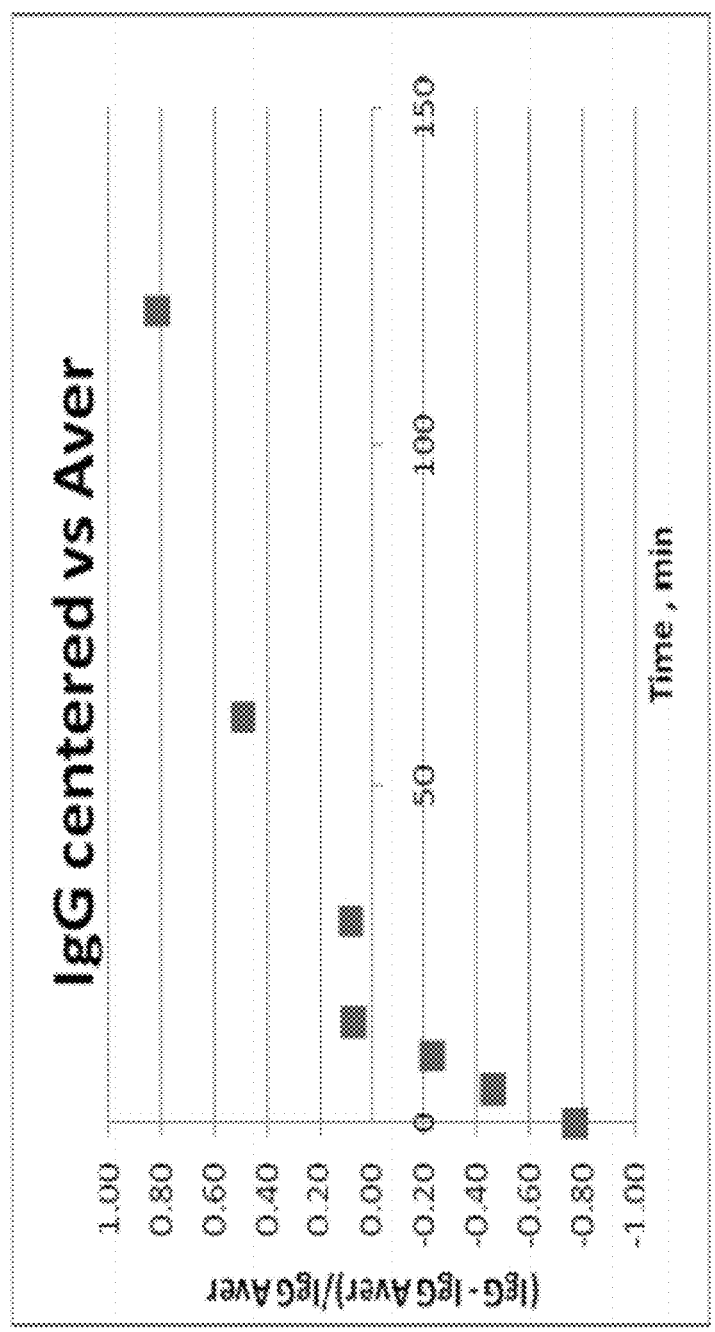
FIG. 9 shows an exemplary graphical representation of IgG Centered vs. Average over time for a Fraction II+III paste being suspended in a buffer.

The concentration of IgG was measured at predetermined times using an Image® 800 Immunochemistry System sold by Beckman Coulter, Inc. The concentration measurements are shown in Table II below with the corresponding IgG Concentration Centered vs. Average values, which were calculated according to Equation 7 and are shown graphically in FIG. 9.

$$\text{IgG Concentration Centered vs. Average} = \frac{(IgG - \overline{IgG})}{\overline{IgG}} \qquad \text{Equation 7}$$

TABLE II

| Time (minutes) | IgG (mg/dL) | IgG Concentration Cent. vs. Avg. |
|---|---|---|
| 0 | 58.8 | −0.77 |
| 5 | 140 | −0.46 |
| 10 | 199 | −0.23 |
| 15 | 277 | 0.07 |
| 30 | 279 | 0.08 |
| 60 | 385 | 0.49 |
| 120 | 469 | 0.82 |

The impedance was monitored at the same predetermined time intervals shown in Table II to determine Re Z and Im Z using an Agilent 4989 precision LCR meter with an ABB TB457 Sterilizable conductivity sensor attached thereto. Additionally, the reference impedance (Re $Z_{Buffer}$ and Im $Z_{Buffer}$) was determined by measuring the complex impedance of the extraction buffer before the Fraction II+III Paste was added. As shown in Equations 8-11, these measurements are subtracted from each Re Z and Im Z measurement to determine ΔRe Z and ΔIm Z.

$$\Delta ReZ = ReZ - ReZ_{Buffer} \qquad \text{Equation 8}$$

$$\Delta\text{Re } Z \text{ Centered vs. Average} = \frac{\Delta\text{Re } Z - \overline{\Delta\text{Re } Z}}{\overline{\Delta\text{Re } Z}} \qquad \text{Equation 9}$$

$$\Delta ImZ = ImZ - ImZ_{Buffer} \qquad \text{Equation 10}$$

$$\Delta\text{Im } Z \text{ Centered vs. Average} = \frac{\Delta\text{Im } Z - \overline{\Delta\text{Im } Z}}{\overline{\Delta\text{Im } Z}} \qquad \text{Equation 11}$$

Figure 10:
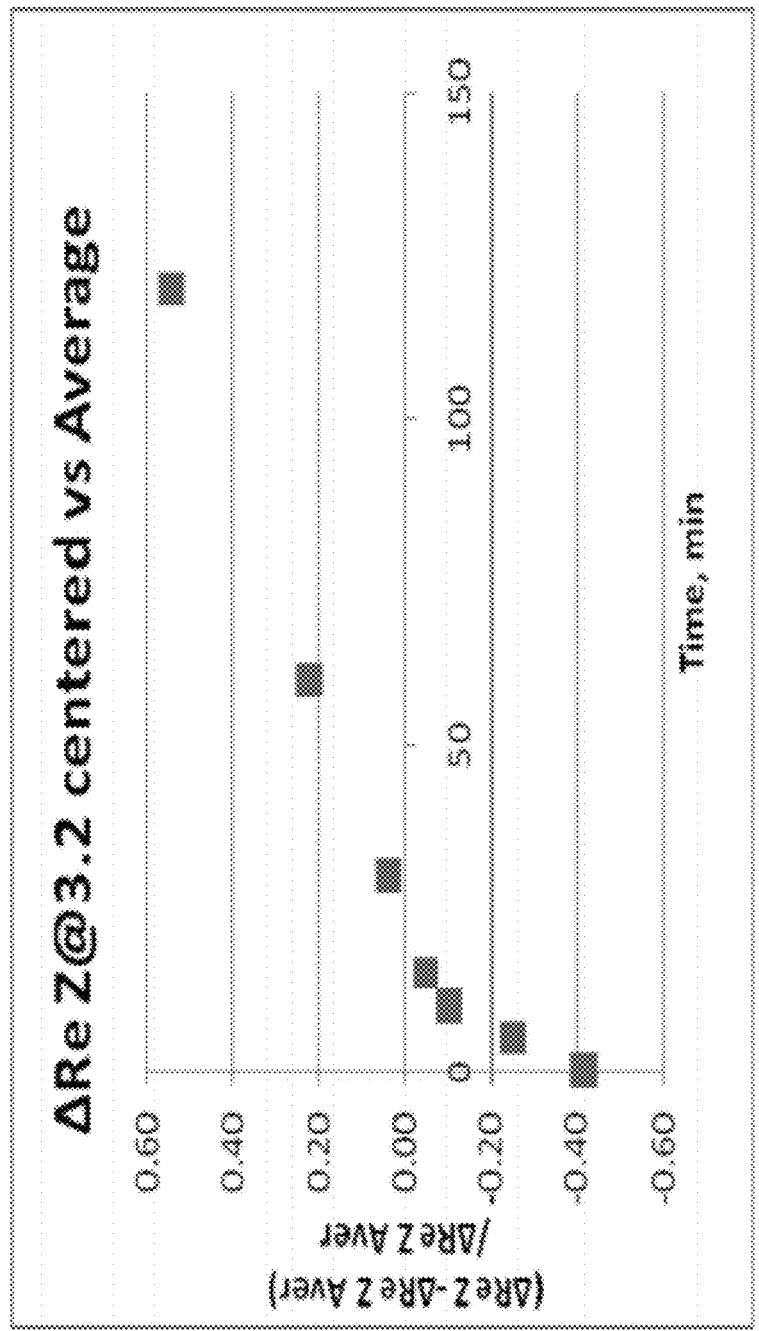
FIG. 10 shows an exemplary graphical representation of ΔRe Z Centered vs. Average over time for a Fraction II+III paste being suspended in a buffer.
Figure 11:
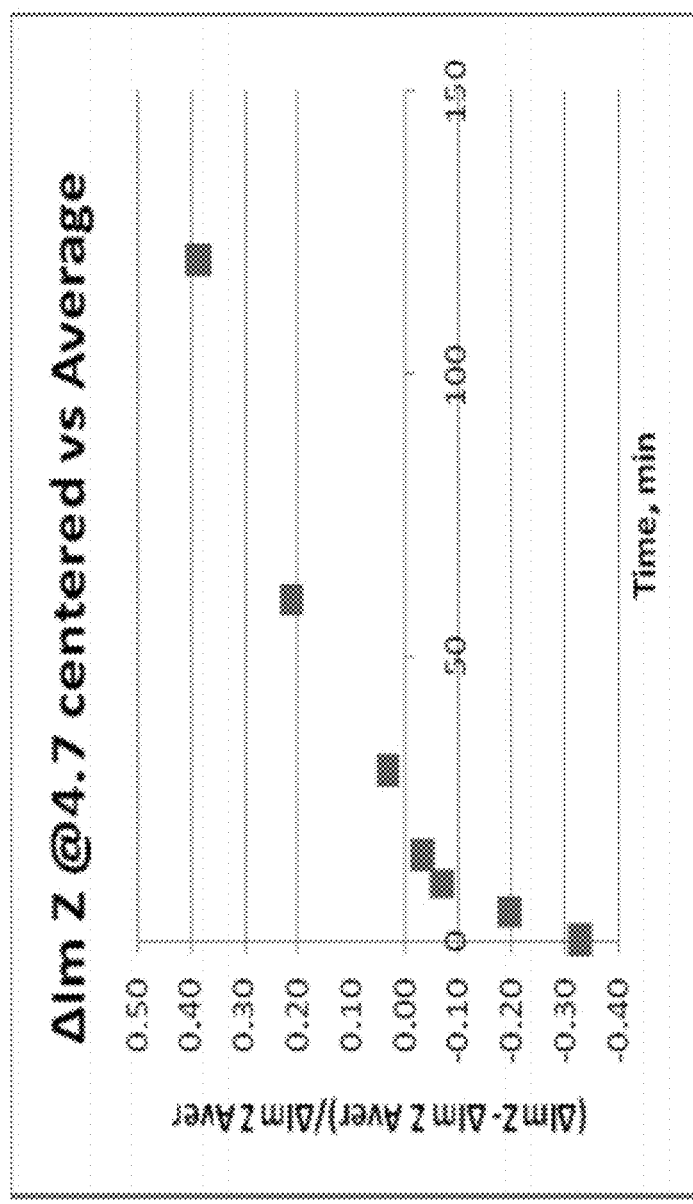
FIG. 11 shows an exemplary graphical representation of ΔIm Z Centered vs. Average over time for a Fraction II+III paste being suspended in a buffer.

The real and imaginary parts of the impedance were determined at frequencies (f), which were previously determined to allow strong correlation of the respective impedance signal to the IgG concentration. The Re Z measurements were taken at a frequency of 1.6 kHz (log(f)=3.2) and the Centered vs. Average values were calculated according to Equation 9 and are shown graphically in FIG. 10. The Im Z measurements were taken at a frequency of 50.2 kHz (log(f)=4.7) and the Centered vs. Average values were calculated according to Equation 11 and are shown graphically in FIG. 11. Table III indicates the results of the measurements and additionally includes ΔIm Z Centered vs. Average and ΔRe Z Centered vs. Average.

TABLE III

| Time (minutes) | Re Z f = 1.6 kHz | Im Z f = 50.2 kHz | ΔRe Z f = 1.6 kHz | ΔIm Z f = 50.2 kHz | ΔRe Z Cent. vs. Avg. f = 1.6 kHz | ΔIm Z Cent. vs. Avg. f = 50.2 kHz |
|---|---|---|---|---|---|---|
| Buffer Measurements | −54.59 | −38.99 | | | | |
| 0 | −45.75 | −25.18 | 8.84 | 13.80 | −0.41 | −0.33 |
| 5 | −43.25 | −22.46 | 11.34 | 16.53 | −0.25 | −0.20 |
| 10 | −41.01 | −19.81 | 13.58 | 19.18 | −0.10 | −0.07 |
| 15 | −40.20 | −19.09 | 14.38 | 19.90 | −0.05 | −0.03 |
| 30 | −38.88 | −17.74 | 15.71 | 21.25 | 0.04 | 0.03 |
| 60 | −36.14 | −14.01 | 18.45 | 24.98 | 0.22 | 0.21 |
| 120 | −31.25 | −10.41 | 23.34 | 28.58 | 0.55 | 0.39 |
| Averages | | | 15.09 | 20.60 | | |

In order to determine optimal frequency range(s) to be implemented, statistical software (Minitab 15.1.1.0) was employed and the following linear regression equations were determined:

$$\Delta IgG = A(f) + B(f) \cdot \Delta ReZ \quad \text{Equation 12}$$

$$\Delta IgG = A'(f) + B'(f) \cdot \Delta ImZ \quad \text{Equation 13}$$

The coefficients A, B, A', B' as well as the corresponding Coefficients of Determination ($R^2$), and Standard Errors of the Regression (S) at different frequencies were solved and are presented in Table IV. The optimal frequency ranges of 1.59, 6.3, 15.9 and 50.2 (shown below in bold) were then defined as those where the $R^2 \geq 95\%$ for either $\Delta Re\,Z$ or $\Delta Im\,Z$, and S is minimal.

TABLE IV

| f (kHz) | Log(f) | ΔRe Z | | | | ΔIm Z | | | |
| --- | --- | --- | --- | --- | --- | --- | --- | --- | --- |
| | | A | B | $R^2$ | S | A' | B' | $R^2$ | S |
| 0.05 | 1.7 | 0.0 | 0.0 | 29.8% | 0.50 | 0.0 | 0.03 | 0.4% | 0.595 |
| 0.1 | 2.0 | 0.0 | 2.1 | 94.4% | 0.15 | 0.0 | 1.29 | 44.5% | 0..444 |
| 0.63 | 2.8 | 0.0 | 1.7 | 94.0% | 0.15 | 0.0 | 3.56 | 81.6% | 0.256 |
| 1.59 | 3.2 | 0.0 | 1.7 | 96.7% | 0.11 | 0.0 | 0.30 | 0.5% | 0.595 |
| 6.3 | 3.8 | 0.0 | 1.87 | 96.0% | 0.12 | 0.0 | 2.67 | 92.9% | 0.16 |
| 15.9 | 4.2 | 0.0 | 1.97 | 95.7% | 0.12 | 0.0 | 2.48 | 95.0% | 0.13 |
| 50.2 | 4.7 | 0.0 | 1.4 | 82.0% | 0.25 | 0.0 | 2.23 | 98.2% | 0.08 |
| 159 | 5.2 | 0.0 | 0.00 | 0.0% | 0.60 | 0.0 | 1.08 | 92.8% | 0.16 |
| 843.4 | 6.0 | 0.0 | 0.7 | 65.5% | 0.35 | 0.0 | 0.07 | 39.2% | 0.47 |

As can be seen from the data of Table IV, both the real and imaginary part of impedance may be correlated to the IgG concentration of a Fraction II+III suspensions. Moreover, the real or imaginary part of impedance may be determined and compared to a reference impedance value to determine the IgG concentration in a Fraction II+III suspension.

Preferably, the frequency range used for impedance measurements should fall within the optimal frequency ranges listed in Table V.

TABLE V

| Impedance | Optimal Frequency Range |
| --- | --- |
| Re Z | about 1.6 kHz to about 16 kHz |
| Im Z | about 16 kHz to about 50 kHz |

Example VII

The impedance (Re Z and/or Im Z) of a biologic fluid was correlated to Human Immunoglobulin G (IgG) concentration at defined frequency ranges during both a filtration and post wash process. A Fraction II+III paste was suspended in an extraction buffer composition. The 1.6 L of suspension was contained in a 10 liter jacketed process tank with water bath for temperature control and the utilized in the filtration and post wash processes.

Figure 12:
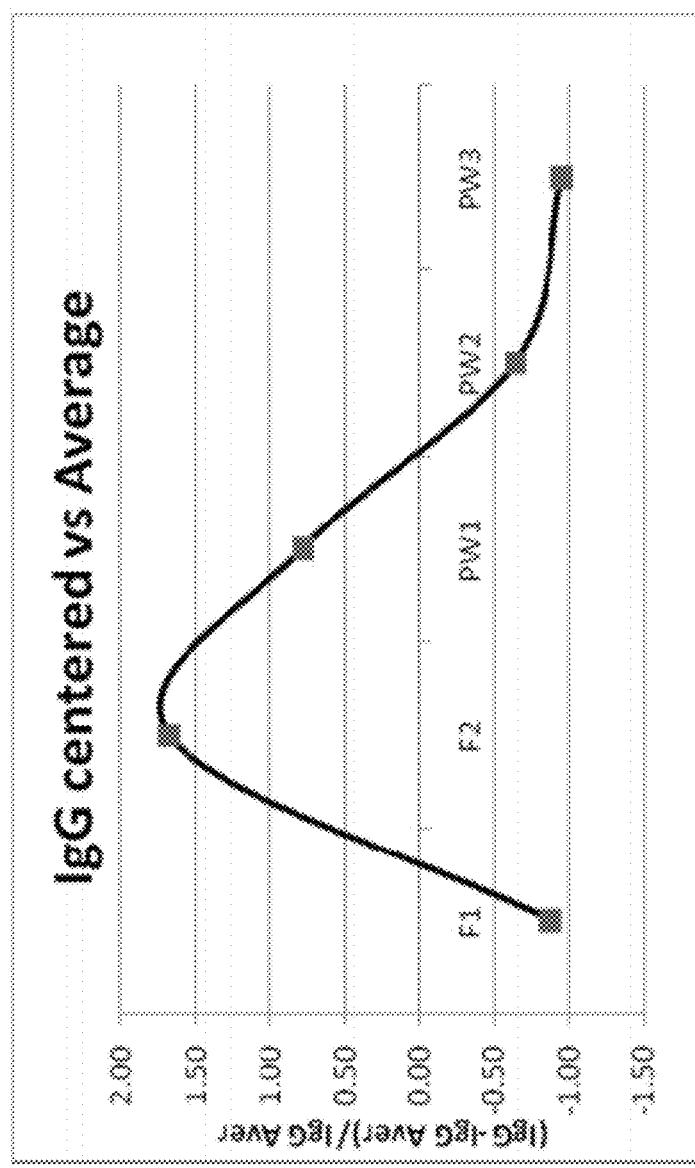
FIG. 12 shows an exemplary graphical representation of IgG Centered vs. Average at multiple steps in a filtration and post-wash process utilizing Fraction II+III.

A 1 L volume sample was collected at each of the process steps (F1, F2, PW1, PW2, PW3) and the IgG concentration as well as Re Z and Im Z were measured at each. The results are shown in Table VI below, with the IgG Centered vs. Average values calculated according to Equation 7. The IgG Centered vs. Average value at each process step is shown graphically in FIG. 12.

TABLE VI

| Process Step | IgG mg/dL | IgG Centered vs. Average |
| --- | --- | --- |
| Filtrate 1 (F1) | 25.3 | −0.87 |
| Filtrate 2 (F2) | 539 | 1.68 |
| Post Wash 1 (PW1) | 359 | 0.78 |
| Post Wash 2 (PW2) | 72.4 | −0.64 |
| Post Wash 3 (PW3) | 10.2 | −0.95 |

Figure 13:
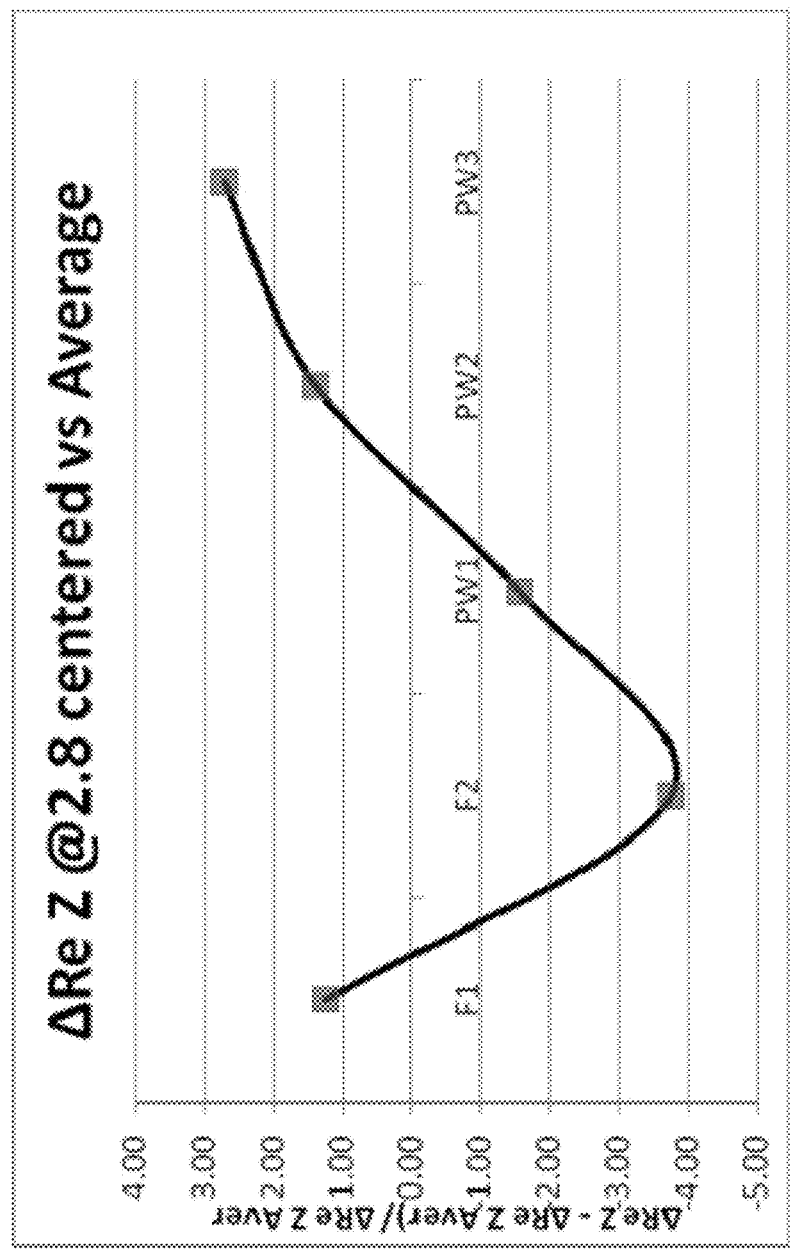
FIG. 13 shows an exemplary graphical representation of ΔRe Z Centered vs. Average at multiple steps in a filtration and post-wash process utilizing Fraction II+III.
Figure 14:
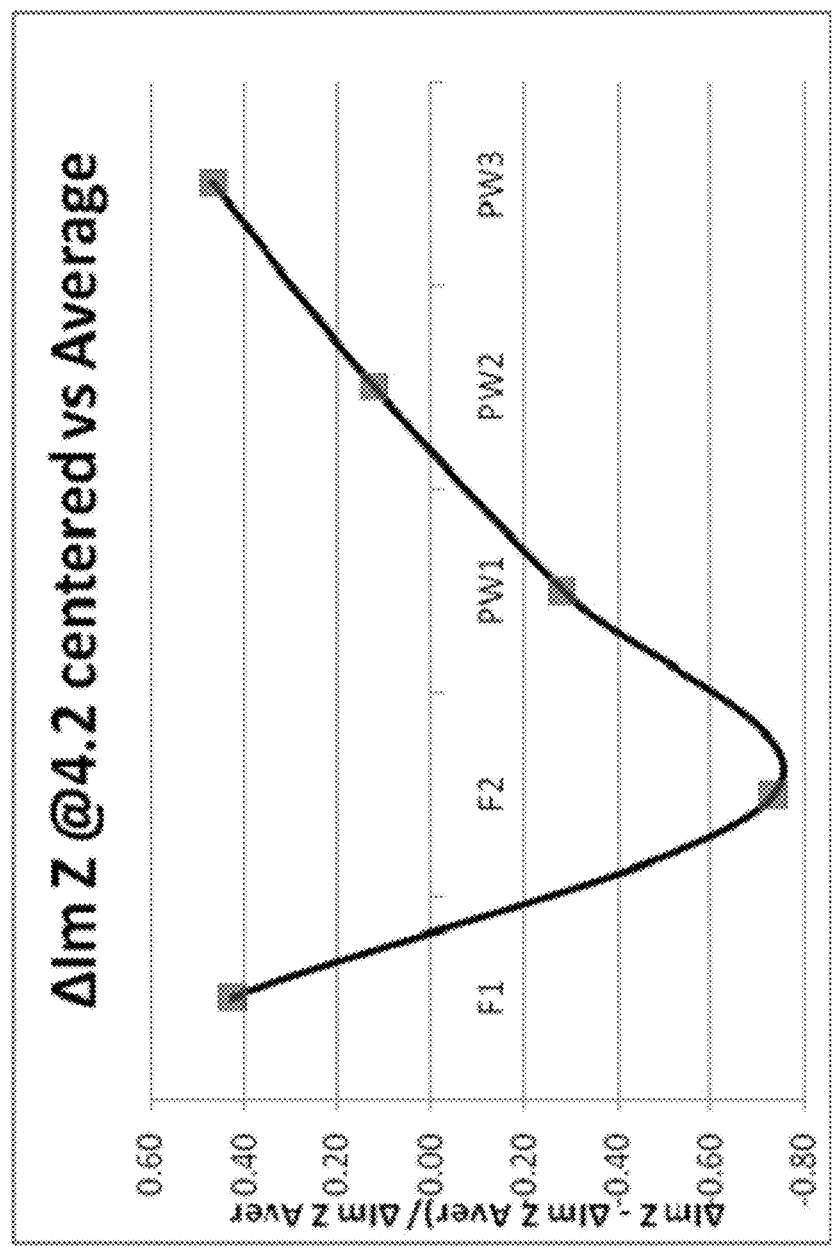
FIG. 14 shows an exemplary graphical representation of ΔIm Z Centered vs. Average at multiple steps in a filtration and post-wash process utilizing Fraction II+III.

The real (Re Z) and imaginary (Im Z) parts of the impedance of each sample were measured at frequencies (f), which were previously determined to allow strong correlation of the respective impedance signal to the IgG concentration. The Re Z measurements were taken at a frequency of 0.63 kHz (log(f)=2.8) and the Centered vs. Average values were calculated according to Equation 9 and are shown graphically in FIG. 13. The Im Z measurements were taken at a frequency of 16 kHz (log(f)=4.2) and the Centered vs. Average values were calculated according to Equation 11 and are shown graphically in FIG. 14. Table VII, below, indicates the results of the measurements and additionally includes the calculated ΔIm Z Centered vs. Average and ΔRe Z Centered vs. Average values.

TABLE VII

| Process Step | Re Z f = 0.63 kHz | Im Z f = 16 kHz | ΔRe Z f = 0.63 kHz | ΔIm Z f = 16 kHz | ΔRe Z Cent. vs. Avg. f = 0.63 kHz | ΔIm Z Cent. vs. Avg. f = 16 kHz |
| --- | --- | --- | --- | --- | --- | --- |
| Buffer | −41.24 | −3.87 | | | | |
| F1 | −49.40 | −10.87 | −8.17 | −8.17 | −8.17 | 0.43 |
| F2 | −31.16 | −5.17 | 10.08 | 10.08 | 10.08 | −0.73 |
| PW1 | −39.20 | −7.40 | 2.04 | 2.04 | 2.04 | −0.28 |
| PW2 | −49.93 | −9.37 | −8.70 | −8.70 | −8.70 | 0.12 |
| PW3 | −54.76 | −11.07 | −13.52 | −13.52 | −13.52 | 0.47 |

Minitab 15.1.1.0 computer software was used to establish the optimal frequency ranges where the correlation between the real and imaginary parts of impedance ($\Delta$Re Z and $\Delta$Im Z) and the measured characteristic ($\Delta$IgG) is strongest. Linear regression equations according to Equations 12 and 13 above were determined, and the coefficients A, B, A', B' as well as the corresponding Coefficients of Determination ($R^2$), and Standard Errors of the Regression (S) at different frequencies are presented in Table VIII. The optimal frequency ranges of 0.63, 6.3 and 15.9 (shown below in bold) were then defined as those where the $R^2 \geq 95\%$ for either $\Delta$Re Z or $\Delta$Im Z, and S is minimal.

TABLE VIII

| f (kHz) | Log(f) | $\Delta$Re Z | | | | $\Delta$Im Z | | | |
|---|---|---|---|---|---|---|---|---|---|
| | | A | B | $R^2$ | S | A' | B' | $R^2$ | S |
| 0.02 | 1.3 | 0.0 | 0.5 | 29.9% | 1.13 | 0.0 | −0.04 | 3.6% | 1.33 |
| 0.05 | 1.7 | 0.0 | 0.1 | 0.7% | 1.35 | 0.0 | −0.02 | 3.4% | 1.33 |
| 0.1 | 2.0 | −1.9 | −1.9 | 67.9% | 0.77 | −0.37 | −0.11 | 89.7% | 0.44 |
| 0.63 | 2.8 | 0.0 | −0.4 | 96.8% | 0.24 | 0.0 | 0.42 | 66.6% | 0.78 |
| 1.59 | 3.2 | 0.0 | −0.14 | 71.1% | 0.73 | 0.0 | −0.21 | 1.2% | 1.35 |
| 6.3 | 3.8 | 0.0 | −0.36 | 94.9% | 0.31 | 0.0 | −2.36 | 88.9% | 0.45 |
| 15.9 | 4.2 | 0.0 | −0.34 | 96.7% | 0.25 | 0.0 | −2.27 | 96.8% | 0.24 |
| 50.2 | 4.7 | 0.0 | −0.13 | 11.0% | 1.28 | 0.0 | 0.85 | 8.1% | 1.30 |
| 159 | 5.2 | 0.0 | 2.71 | 77.6% | 0.64 | 0.0 | −1.64 | 93.5% | 0.35 |
| 251.8 | 5.4 | 0.0 | −4.9 | 41.0% | 1.04 | 0.0 | −1.33 | 43.9% | 1.02 |
| 399.1 | 5.6 | 0.0 | −3.00 | 21.7% | 1.19 | 0.0 | 0.34 | 49.3% | 0.97 |
| 843.4 | 6.0 | 0.0 | −2.29 | 35.9% | 1.09 | 0.0 | 0.91 | 1.4% | 1.35 |

As shown in Tables VII and VIII, both the real and/or imaginary parts of impedance may be employed for the control and/or monitoring of IgG concentration during a filtration and/or post wash process steps of Fraction II+III paste suspensions. The impedance measurements may be correlated with the data provided herein to extrapolate the IgG concentration during the filtration and/or post wash processes steps of Fraction II+III paste. According to the data provided herein, the optimal frequency ranges for measuring IgG concentrations are shown in Table IX.

TABLE IX

| Impedance | Optimal Frequency Range |
|---|---|
| Re Z | about 0.6 kHz |
| | about 1.6 kHz to about 16 kHz |
| Im Z | about 16 kHz |

Example VIII

In one exemplary embodiment, ranges of reference impedance values were measured for a 5% by volume albumin solution at a number of different frequencies and alcohol concentrations. A 95% by volume ethanol solution was incrementally added to a solution of 1.6 kg of water and 0.4 kg of albumin in a 10 L jacketed tank in a water bath. The ethanol solution was added at a temperature of −1° C. Multiple impedance measurements at a number of frequencies were taken and stored in a general purpose computer when the solution reached 5% ethanol by volume. These steps were repeated at 10% ethanol by volume, 15% ethanol by volume, 20% ethanol by volume, 25% ethanol by volume and 30% ethanol by volume. The reference impedance values were plotted and compared to determine the effect of alcohol concentration on the impedance of the albumin solution.

Figure 16:
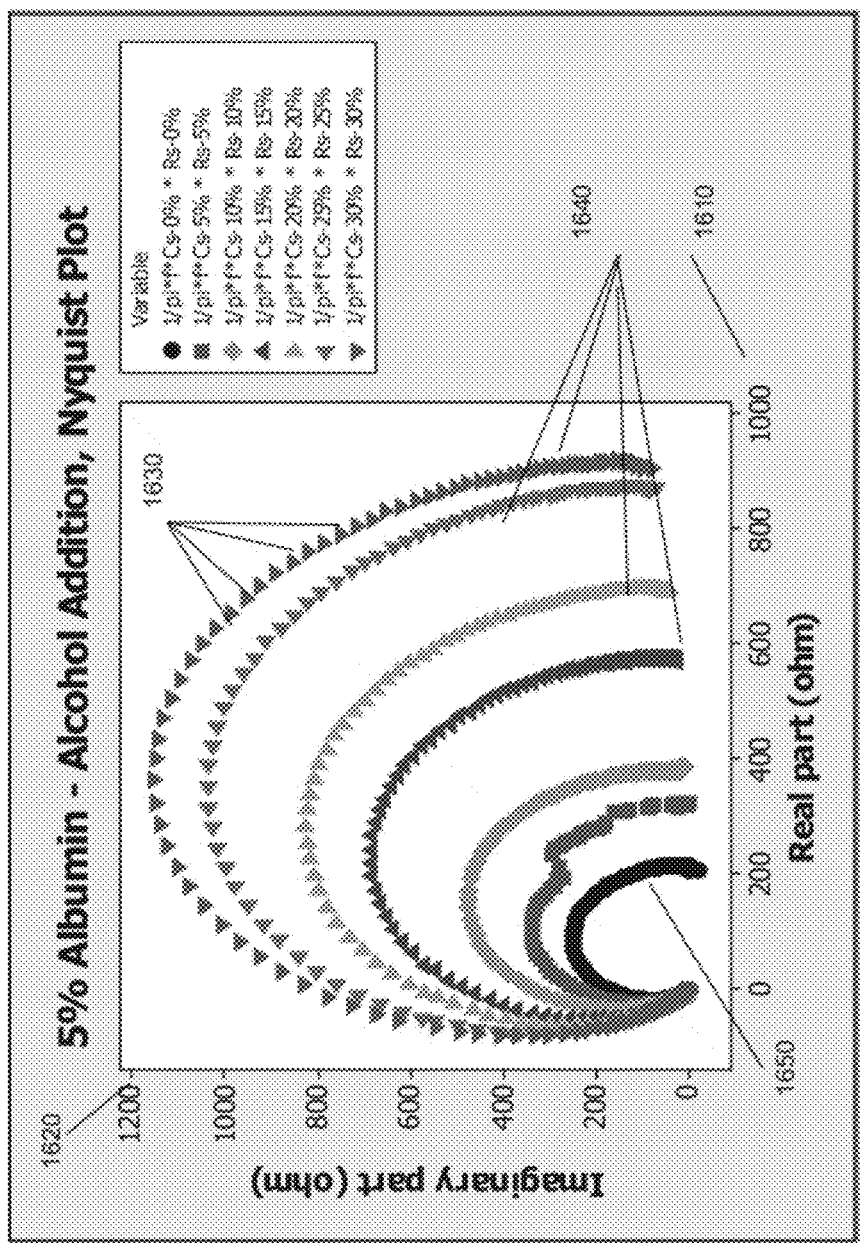
FIG. 16 illustrates an exemplary Nyquist plot showing that the impedance of an albumin solution may be correlated to the alcohol concentration of the solution.

The resulting Nyquist Plot is shown in FIG. 16, wherein the real part of the impedance 1610 is plotted against the imaginary part of the impedance 1620 of the solution at multiple frequencies 1630 ranging from 1 KHz to 2 MHz and multiple alcohol concentrations 1640 ranging from 5% by volume to 30% by volume. The real 1610 and imaginary 1620 parts of the impedance may be determined at any number of frequencies 1630 between 1 KHz to 2 MHz and the measured impedance values may be stored in, for example, a database on a general purpose computer for comparison to measured impedance values. For example, the Nyquist Plot of FIG. 16 may be used to extrapolate a concentration of alcohol in a sample solution, having otherwise the same or similar composition, based on impedance measurements of such a solution at frequencies ranging from 1 KHz to 2 MHz. It is contemplated that impedance values of any solution containing alcohol may be correlated using a Nyquist plot similar to that shown in FIG. 16.

Optimal frequency ranges for correlating the alcohol concentration to the real part of impedance were also determined at varying ethanol concentrations. The real part of the impedance (Re Z) was measured at each of alcohol concentrations shown in Table X using an Agilent 4989 precision LCR meter having an ABB Model TB457 sterilizable conductivity sensor attached thereto.

TABLE X

| Alcohol Concentration % by volume | Re Z f = 0.63 kHz | $\Delta$Re Z f = 0.63 kHz | $\Delta$Re Z Cent. vs. Avg. f = 0.63 kHz |
|---|---|---|---|
| 0 | −208 | | |
| 5 | −292 | −83.6 | .209 |
| 10 | −380 | −171 | .427 |
| 15 | −569 | −360 | .897 |
| 20 | −679 | −471 | 1.17 |
| 25 | −853 | −645 | 1.61 |
| 30 | −885 | −676 | 1.69 |

Figure 15:
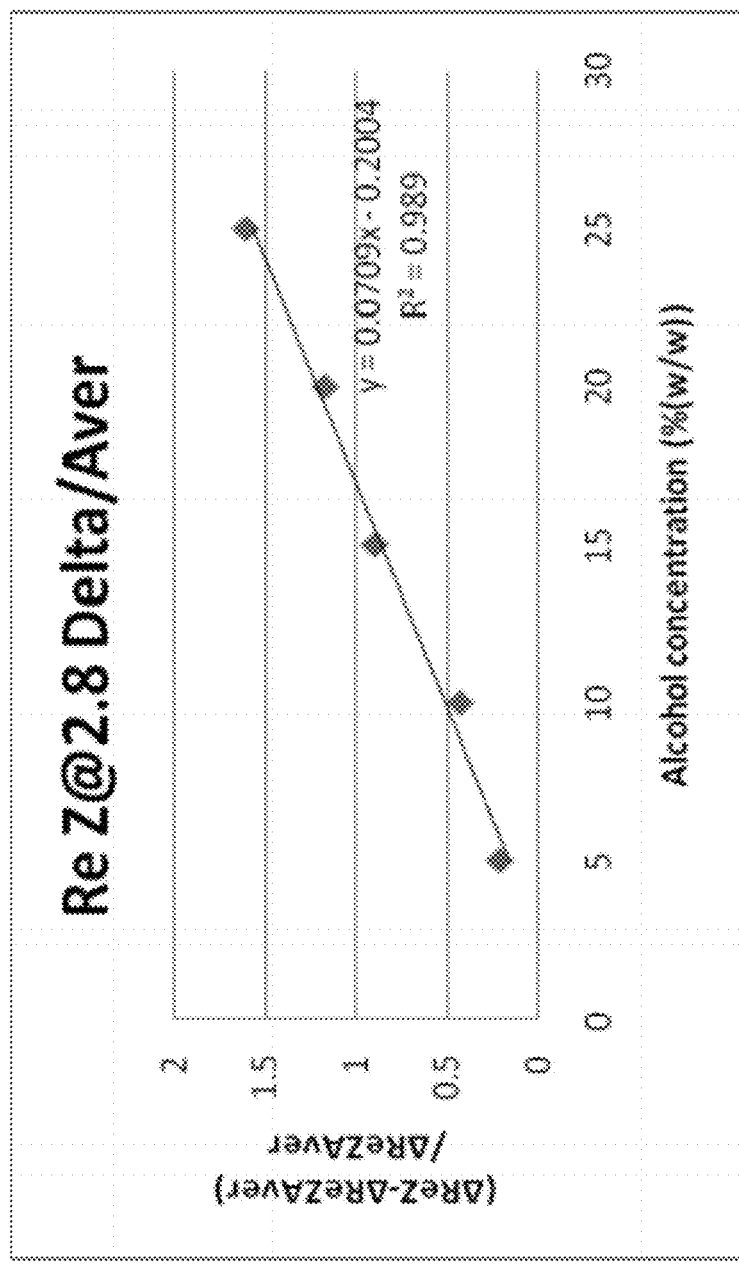
FIG. 15 shows an exemplary graphical representation of ΔRe Z Centered vs. Average for a 5% albumin solution undergoing an alcohol addition process.

The $\Delta$Re Z and $\Delta$Re Z Centered vs. Average shown in Table X were calculated using Equations 14 and 15 and are shown graphically in FIG. 15.

$$\Delta ReZ = ReZ - ReZ_0, \text{ where } Re Z_0 = Re Z \text{ at 0\% Alcohol} \quad \text{Equation 14}$$

$$\Delta Re\ Z \text{ Centered vs. Average} = \frac{\Delta Re\ Z - \overline{\Delta Re\ Z}}{\overline{\Delta Re\ Z}} \quad \text{Equation 15}$$

Minitab 15.1.1.0 computer software was used to establish the optimal frequency ranges where the correlation between the ΔRe Z and the alcohol concentration (AC) is strongest. A linear regression equation according to Equation 10 was determined, and the coefficients A, B as well as the corresponding Coefficients of Determination ($R^2$), and Standard Errors of the Regression (S) at different frequencies are presented in Table XI. The optimal frequency ranges of 0.02, 0.63, 1.59, 6.3, 15.9, and 843.4 (shown below in bold) were defined as those where the $R^2 \geq 95\%$ for ΔRe Z, and S is minimal.

TABLE XI

| f (kHz) | Log(f) | ΔRe Z | | | |
|---|---|---|---|---|---|
| | | A | B | $R^2$ | S |
| 0.02 | 1.3 | 18.65 | 16.14 | 96.0% | 1.8 |
| 0.05 | 1.7 | 16.38 | 6.13 | 68.5% | 5.1 |
| 0.1 | 2.0 | 17.39 | 11.27 | 80.1% | 4.1 |
| 0.63 | 2.8 | 2.96 | 13.95 | 98.9% | 0.96 |
| 1.59 | 3.2 | 2.48 | 14.50 | 98.1% | 1.26 |
| 6.3 | 3.8 | 2.57 | 14.38 | 98.1% | 1.26 |
| 15.9 | 4.2 | 1.32 | 15.27 | 98.2 | 1.23 |
| 50.2 | 4.7 | 18.54 | -0.85 | 45.8% | 6.7 |
| 159 | 5.2 | -6.54 | 22.50 | 91.3 | 2.69 |
| 843.4 | 6.0 | -19.39 | 36.40 | 97.6 | 1.47 |

As shown in Tables X and XI, the real part of the impedance may be employed for the monitoring and/or control of alcohol concentration during alcohol addition to albumin containing solutions The optimal frequency ranges found for measuring alcohol addition to albumin containing solutions are shown in Table XII.

TABLE XII

| Impedance | Optimal Frequency Range |
|---|---|
| Re Z | about 0.02 kHz |
| | about 0.63 kHz to about 16 kHz |
| | about 843 kHz |

Example IX

The complex impedance was correlated to alcohol concentration of a cryo-poor plasma at certain frequencies during an alcohol addition process. A 95% by volume ethanol solution was incrementally added to a solution of 4.24 g of 5M acetic acid and 3.43 kg of cryo-poor plasma in a 10 L jacketed tank in a water bath. About 0.237 kg of the ethanol solution was added over a 1.5 hour period at a temperature of –2° C. to produce a 8% by volume alcohol mixture. Additionally, 0.018 kg of a buffer was added. The real part of the impedance was determined at each alcohol concentration shown in Table XIII using an Agilent 4989 precision LCR meter having an ABB Model TB457 sterilizable conductivity sensor attached thereto. Moreover, the alcohol concentration was increased from 8% to 20% by volume over an additional 5 hours, and additional impedance measurements were taken.

TABLE XIII

| Alcohol Concentration % by volume | Re Z f = 0.63 kHz | ΔRe Z f = 0.63 kHz | ΔRe Z Cent. vs. Avg. f = 0.63 kHz |
|---|---|---|---|
| 0 | -31.90 | | |
| 1.2 | -33.97 | -2.063 | -0.9289 |
| 2.4 | -38.68 | -6.77 | -0.7666 |
| 5.1 | -45.71 | -13.81 | -0.5241 |
| 6.5 | -47.82 | -15.91 | -0.4516 |
| 8.4 | -52.48 | -20.57 | -0.2910 |
| 11.5 | -60.99 | -29.08 | 0.0023 |
| 14.7 | -70.78 | -38.87 | 0.3398 |
| 17.5 | -81.93 | -50.02 | 0.7243 |
| 20.3 | -85.34 | -53.43 | 0.8417 |
| 21.8 | -91.54 | -59.63 | 1.0556 |

The ΔRe Z and ΔRe Z Centered vs. Average shown in Table XIII were calculated using Equations 14 and 15 and are shown graphically in FIG. 17.

Minitab 15.1.1.0 computer software was used to establish the optimal frequency ranges where the correlation between the ΔRe Z and the alcohol concentration (AC) is strongest. A linear regression equation according to Equation 12 was determined, and the coefficients A, B as well as the corresponding Coefficients of Determination ($R^2$), and Standard Errors of the Regression (S) at different frequencies are presented in Table XIV. The optimal frequency ranges of 0.05, 0.1, 1.59, 6.3, 15.9, 50.2, and 159 (shown below in bold) were defined as those where the $R^2 \geq 95\%$ for ΔRe Z, and S is minimal.

TABLE XIV

| f (kHz) | Log (f) | ΔRe Z | | | |
|---|---|---|---|---|---|
| | | A | B | R2 | S |
| 0.02 | 1.3 | 10.94 | 13.15 | 83.4% | 3.18 |
| 0.05 | 1.7 | 10.94 | 8.50 | 97.1% | 1.32 |
| 0.1 | 2.0 | 10.93 | 10.97 | 98.9% | 0.84 |
| 0.63 | 2.8 | 10.94 | 9.85 | 83.8% | 3.15 |
| 1.59 | 3.2 | 10.92 | 11.07 | 99.5% | 0.57 |
| 6.3 | 3.8 | 10.94 | 10.60 | 99.5% | 0.58 |
| 15.9 | 4.2 | 10.94 | 10.45 | 99.5% | 0.55 |
| 50.2 | 4.7 | 10.94 | 10.77 | 99.5% | 0.58 |
| 159 | 5.2 | 10.94 | 12.09 | 97.4% | 1.25 |
| 843.4 | 6.0 | 10.94 | 2.25 | 63.0% | 4.77 |

As shown in the data provided in Tables XVII and XIV, it was found that impedance may be used to monitor and/or control alcohol concentration during alcohol addition to a cryo-poor plasma solution. The optimal frequency ranges found for measuring alcohol addition to a cryo-poor plasma solution are shown in Table XV.

TABLE XV

| Impedance | Optimal Frequency Range |
|---|---|
| Re Z | about 0.02 kHz |
| | about 0.63 kHz to about 16 kHz |
| | about 843 kHz |

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

We claim:

1. A method for preparing a protein suspension having an impedance within a target reference range of impedance values, said method comprising:
   admixing a protein solid or paste with a solvent to form a protein suspension;
   monitoring the impedance of said protein suspension during said admixing step;
   comparing said impedance to a target reference range of impedance values;
   continuing said admixing, monitoring and comparing steps until an impedance value is obtained for said protein suspension within the target reference range of impedance values; and
   removing remaining protein solid or paste from said protein suspension when said impedance value within the target reference range of impedance values is obtained.

2. The method according to claim 1, wherein said protein solid or paste is a fractionated plasma intermediate or a fractionated plasma product from a plasma fractionation process.

3. The method according to claim 2, wherein said plasma fractionation process comprises a Cohn process, an Oncley process, a Kistler process, a Teschner process or a combination thereof.

4. The method according to claim 3, wherein said plasma fractionation process is a Cohn process and said fractionated plasma intermediate is selected from the group consisting of Fraction I, Fraction II+III, Fraction III, Fraction IV-1, Fraction IV-4, and Fraction V from said Cohn process.

5. The method according to claim 3, wherein said plasma fractionation process is an Oncley process and said fractionated plasma intermediate is selected from the group consisting of Fraction II+IIIW, Fraction II, and Fraction III of said Oncley process.

6. The method according to claim 3, wherein said plasma fractionation process is a Kistler process and said fractionated plasma intermediate is selected from the group consisting of Precipitate A, Precipitate B, Precipitate IV, Precipitate C, and Precipitate D of said Kistler process.

7. The method according to claim 3, wherein said plasma fractionation process is a Techsner process and said fractionated plasma intermediate comprises Precipitate G of said Teschner process.

8. The method according to claim 1, wherein said target reference range of impedance values corresponds to a target degree of uniformity of said protein suspension.

9. The method according to claim 1 further comprising:
   notifying an operator when said impedance of said protein suspension is within the target reference range of impedance values.

10. The method according to claim 1 further comprising:
    automatically filtering said protein suspension when said impedance of said protein suspension is within the target reference range of impedance values.

11. The method of claim 1, wherein the protein suspension is prepared in an amount of 1.6 L to 10 L.

12. The method of 1, wherein the protein suspension is prepared on at least a liter-scale.

13. A method for controlling a protein separation process for separating a protein from a biologic fluid, said method comprising:
    obtaining an impedance measurement of said biologic fluid from a step of said protein separation process;
    determining an amount of modification of a parameter of said biologic fluid that modifies solubility of said protein in said biologic fluid needed to cause the impedance measurement of said biologic fluid to be within an acceptable tolerance of a target impedance value, said parameter selected from the group consisting of solute concentration, solvent concentration, pH, ionic strength, temperature, density, flow rate, and viscosity;
    bringing about an increase or decrease in solubility of said protein in said biologic fluid by adjusting said parameter that modifies solubility of said protein in said biologic fluid by said amount of modification to bring said impedance value within said acceptable tolerance of said target impedance value; and
    separating said insoluble protein from said soluble protein remaining in said biologic fluid when impedance of said biologic fluid is within said acceptable tolerance; thereby controlling said protein separation process.

14. The method according to claim 13, wherein said step of said protein separation process comprises precipitating said protein from said biologic fluid.

15. The method according to claim 13, wherein said step of said protein separation process comprises purifying or concentrating said protein.

16. The method according to claim 13, wherein said determining step comprises providing a notification to an operator when said measurement deviates from said target impedance value by more than said acceptable tolerance.

17. The method according to claim 13, wherein said adjusting step comprises triggering an analysis of said biologic fluid.

18. The method according to claim 13, wherein said biologic fluid is selected from the group consisting of blood plasma, fractionated plasma intermediates, protein solutions and suspensions, and cell culture suspensions.

19. The method according to claim 18, wherein said biologic fluid is a blood plasma or a fractionated plasma intermediate.

20. The method according to claim 13, wherein the protein is a fractionated plasma product.

21. The method according to claim 20, wherein the fractionated plasma product is selected from the group consisting of albumin, alpha1-proteinase inhibitor, antihemophilic factor, von Willebrand factor complex, anti-inhibitor coagulant complex, antithrombin, C1 esterase inhibitor, coagulation factors, fibrin, fibrinogen, immunoglobulins, protein C concentrate, and thrombin.

22. The method according to claim 13, wherein said adjusting step comprises automatically adjusting said parameter when said measurement deviates from said target impedance value by more than said acceptable tolerance.

23. The method according to claim 22, wherein said adjusting step is performed substantially in real-time.

24. The method according to claim 22, wherein said adjusting step is performed in real-time.

25. The method according to claim 13, wherein said step of said protein separation process comprises a continuous flow process.

26. The method according to claim 25, wherein said biologic fluid is an in-line biologic fluid from said continuous flow process.

27. The method according to claim 13, wherein said step of said protein separation comprises a batch process.

28. The method according to claim 27, wherein said biologic fluid is a batch mixture from said batch process.

29. The method according to claim 13, wherein said step of said protein separation process comprises a filtration process.

30. The method of claim 13, wherein the biologic fluid is used in an amount of 1.6 L to 10 L.

31. The method of claim 13, wherein the protein separation process is performed on at least a liter-scale.

32. A method for separating a protein from a biologic fluid to a targeted degree, the method comprising:
adjusting a parameter of said biologic fluid to modify solubility of said protein in said biologic fluid, said parameter selected from the group consisting of solute concentration, solvent concentration, pH, ionic strength, temperature, density, flow rate, and viscosity;
monitoring impedance of the biologic fluid during said adjusting step;
comparing said impedance to a target impedance value corresponding to a target degree of separation of said protein from said biologic fluid;
bringing about an increase or decrease in solubility of said protein in said biologic fluid by further modifying said parameter when said impedance deviates from said target impedance value by more than an acceptable tolerance to bring said impedance value within said acceptable tolerance of said target impedance value; and
separating said insoluble protein from said soluble protein remaining in said biologic fluid when impedance of said biologic fluid is within said acceptable tolerance;
thereby effecting a protein separation to said targeted degree.

33. The method according to claim 32, wherein said modifying step comprises further modifying said parameter when said impedance deviates from said target impedance value by at least 5%.

34. The method according to claim 32, wherein said modifying step comprises further modifying said parameter when said impedance deviates from said target impedance value by at least 1.0%.

35. The method according to claim 32, wherein said modifying step comprises further modifying said parameter when said impedance deviates from said target impedance value by at least 0.5%.

36. The method according to claim 32, wherein said modifying step comprises providing a notification to an operator when said impedance deviates from said target impedance value by more than said acceptable tolerance.

37. The method according to claim 32, wherein said modifying step further comprises triggering an analysis of said biologic fluid.

38. The method according to claim 32, wherein said biologic fluid is selected from the group consisting of blood plasma, fractionated plasma intermediates, protein solutions and suspensions, and cell culture suspensions.

39. The method according to claim 38, wherein said biologic fluid is a blood plasma or a fractionated plasma intermediate.

40. The method according to claim 32, wherein the protein is a fractionated plasma product.

41. The method according to claim 40, wherein the fractionated plasma product is selected from the group consisting of albumin, alpha1-proteinase inhibitor, antihemophilic factor, von Willebrand factor complex, anti-inhibitor coagulant complex, antithrombin, C1 esterase inhibitor, coagulation factors, fibrin, fibrinogen, immunoglobulin, protein C concentrate, and thrombin.

42. The method according to claim 32, wherein said modifying step comprises automatically modifying said parameter when said impedance deviates from said target impedance value by more than said acceptable tolerance.

43. The method according to claim 42, wherein said modifying step is performed substantially in real-time.

44. The method according to claim 43, wherein said modifying step is performed in real-time.

45. The method according to claim 32, wherein said modifying step comprises:
determining an amount of modification of said parameter needed to cause the impedance of said biologic fluid to be at or about said target impedance value when said impedance deviates from said target impedance value by more than said acceptable tolerance; and
modifying the parameter by said amount of modification.

46. The method of claim 32, wherein the biologic fluid is used in an amount of 1.6 L to 10 L.

47. The method of claim 32, wherein the protein separation is performed on at least a liter-scale.

* * * * *